US009562076B2

(12) United States Patent
Mier et al.

(10) Patent No.: US 9,562,076 B2
(45) Date of Patent: *Feb. 7, 2017

(54) HYDROPHOBIC MODIFIED PRES-DERIVED PEPTIDES OF HEPATITIS B VIRUS (HBV) AND THEIR USE AS HBV AND HDV ENTRY INHIBITORS

(75) Inventors: Walter Mier, Bensheim (DE); Stephan Urban, Neustadt (DE)

(73) Assignee: RUPRECHT-KARLS-UNIVERSITÄT-HEIDELBERG (Rektorat), Heidelberg (DE)

( * ) Notice: Subject to any disclaimer, the term of this patent is extended or adjusted under 35 U.S.C. 154(b) by 369 days.

This patent is subject to a terminal disclaimer.

(21) Appl. No.: 12/863,663

(22) PCT Filed: Jan. 26, 2009

(86) PCT No.: PCT/EP2009/000476
§ 371 (c)(1),
(2), (4) Date: Oct. 11, 2010

(87) PCT Pub. No.: WO2009/092611
PCT Pub. Date: Jul. 30, 2009

(65) Prior Publication Data
US 2011/0020397 A1    Jan. 27, 2011

(30) Foreign Application Priority Data

Jan. 25, 2008 (WO) ................. PCT/EP2008/000591

(51) Int. Cl.
| | | |
|---|---|---|
| A61K 39/29 | (2006.01) |
| C07K 7/08 | (2006.01) |
| C07K 14/02 | (2006.01) |
| A61P 31/20 | (2006.01) |
| C07K 14/005 | (2006.01) |
| A61K 47/48 | (2006.01) |
| A61K 39/12 | (2006.01) |
| A61K 38/00 | (2006.01) |

(52) U.S. Cl.
CPC ............ *C07K 14/005* (2013.01); *A61K 39/12* (2013.01); *A61K 39/292* (2013.01); *A61K 47/48023* (2013.01); *A61K 47/48038* (2013.01); *A61K 47/48053* (2013.01); *A61K 47/48123* (2013.01); *A61K 38/00* (2013.01); *C12N 2730/10122* (2013.01); *C12N 2730/10134* (2013.01)

(58) Field of Classification Search
CPC .............................. A61K 38/00; C12N 15/111
See application file for complete search history.

(56) References Cited

U.S. PATENT DOCUMENTS

| | | | | |
|---|---|---|---|---|
| 5,929,220 A * | 7/1999 | Tong et al. | .................. | 536/23.1 |
| 6,258,937 B1 | 7/2001 | Tong et al. | | |
| 6,589,534 B1 * | 7/2003 | Shaul et al. | ............... | 424/227.1 |
| 7,476,390 B2 * | 1/2009 | Apt et al. | .................... | 424/218.1 |
| 7,892,754 B2 * | 2/2011 | Gripon et al. | ................. | 435/7.1 |
| 2005/0053914 A1 * | 3/2005 | Gripon et al. | ..................... | 435/5 |

FOREIGN PATENT DOCUMENTS

| | | |
|---|---|---|
| CN | 1733798 A | 2/2006 |
| CN | 101045156 A | 3/2007 |
| EP | 1 281 761 A1 | 2/2003 |
| EP | 0 563 093 B2 | 10/2007 |

OTHER PUBLICATIONS

Petersen (Journal of Hepatology, Apr. 2006, p. 16 in IDS on Sep. 10, 2010.*
Gripon et al. (Journal of Virology, 2005, vol. 79, p. 1613-1622 in IDS on Sep. 10, 2010).*
Barrera, Azeneth et al., "Mapping of the Hepatitis B Virus Pre-S1 Domain Involved in Receptor Recognition," *Journal of Virology* (Aug. 2005) 79(15):9786-9798.
Chan, Henry Lik-Yuen et al., "Hepatocellular Carcinoma and Hepatitis B Virus," *Seminars in Liver Disease* (2006) 26(2):153-161.
Chen, Jinsong et al., "Improved multiplex-PCR to identify hepatitis B virus genotypes A-F and subgenotypes B1, B2, C1 and C2," *Journal of Clinical Virology* (2007) 38:238-243.
Dandri, Maura et al., "Hepatitis B Virus cccDNA Clearance: Killing or Curing?" *Hepatology* (Dec. 2005) 1453-1455.
Dandri, Maura et al., "Chronic infection with hepatitis B viruses and antiviral drug evaluation in uPA mice after liver repopulation with tupaia hepatocytes," *Journal of Hepatology* (2005) 42:54-60.
Engelke, Matthias et al., "Characterization of a Hepatitis B and Hepatitis Delta Virus Receptor Binding Site," *Hepatology* (2006) 43(4):750-760.
Freireich, Emil J. et al., "Quantitative Comparison of Toxicity of Anticancer Agents in Mouse, Rate, Hamster, Dog, Monkey, and Man," *Cancer Chemotherapy Reports* (May 1966) (50(4):219-244.
Gausepohl, H. et al., "Asparagine coupling in Fmoc solid phase peptide synthesis," *Int. J. Peptide Protein Res.* (1980) 34:287-294.
Glebe, Dieter et al., "Mapping of the Hepatitis B Virus Attachment Site by Use of Infection-Inhibiting preS1 Lipopeptides and Tupaia Hepatocytes," *Gastroenterology* (2005) 129:234-245.
Glebe, D. "Attachment sites and neutralizing epitopes of hepatitis B virus," *Minvera Gastroenterol Dietol* (2006) 52:3-21.
Glebe, Dieter et al., "Viral and cellular determinants involved in hepadnaviral entry," *World J Gastroenterol* (Jan. 7, 2007) 13(1):22-38.
Gripon, P. et al., "Myristylation of the Hepatitis B Virus Large Surface Protein Is Essential for Viral Infectivity," *Virology* (1995) 213:292-299.
Gripon, Philippe et al., "Infection of a human hepatoma cell line by hepatitis B virus," *PNAS* (Nov. 26, 2002) 99(24):15655-15660.
Gripon, Philippe et al., "Efficient Inhibition of Hepatitis B Virus Infection by Acylated Peptides Derived from the Large Viral Surface Protein," *Journal of Virology* (Feb. 2005) 79(3):1613-1622.
Krieger, David E. et al., "Affinity purification of synthetic peptides," *Proc. Natl. Acad. Sci. USA* (Sep. 1976) 73(9):3160-3164.

(Continued)

*Primary Examiner* — Agnieszka Boesen
(74) *Attorney, Agent, or Firm* — Jones Day

(57) ABSTRACT

The present invention relates to hydrophobic modified preS-derived peptides of hepatitis B virus (HBV) which are derived from a HBV preS consensus sequence and are N-terminal preferably acylated and optional C-terminal modified. These hydrophobic modified preS-derived peptides of HBV are very effective HBV entry inhibitors as well as HDV entry inhibitors and are, thus, suitable for the inhibition of HBV and/or HDV infection, prevention of primary HBV and/or HDV infection as well as treatment of (chronic) hepatitis B and/or D. The present invention further relates to pharmaceutical and vaccine compositions comprising these hydrophobic modified preS-derived peptides of HBV.

41 Claims, 12 Drawing Sheets

(56) References Cited

OTHER PUBLICATIONS

Le Seyec, J. et al., "Infection Process of the Hepatitis B Virus Depends on the Presence of a Defined Sequence in the Pre-S1 Domain," *Journal of Virology* (Mar. 1999) 73(3):2052-2057.

Locarnini, Stephen et al., "Management of antiviral resistance in patients with chronic hepatitis B," *Antiviral Therapy* (2004) 9:679-693.

Nassal, M., "Hepatitis B Virus Morphogenesis," *Curr Top Microbiol Immunol.* (1996) 214:297-337.

Petersen, J. et at "In Vivo Inhibition of HBV Infection by Acylated preS Peptides in the Urokinase-Type Plasminogen Activator (uPA) Mouse Model," *Journal of Hepatology* (Apr. 27, 2006) 44(2):S16.

Petersen, Joerg et al., "Prevention of hepatitis B virus infection in vivo by entry inhibitors derived from the large envelope protein," *Nature Biotechnology* (Mar. 2008) 26(3)335-341.

Root, Michael J. et al., "HIV-1 gp41 as a Target for Viral Entry Inhibition," *Current Pharmaceutical Design* (2004) 10:1805-1825.

Seeger, Christoph et al., "Hepatitis B Virus Biology," *Microbiology and Molecular Biology Reviews* (Mar. 2000) 64(1):51-68.

Shepard, Colin W. et al., "Hepatitis B Virus Infection: Epidemiology and Vaccination," *Epidemiol Rev* (2006) 28:112-125.

Taylor, John M., "Hepatitis delta virus," *Virology* (2006) 344:71-76.

Zoulim, Fabien, "Antiviral therapy of chronic hepatitis B," *Antiviral Research* (2006) 71:206-215.

Petersen et al., Interference with HBV Receptor Interaction by Acylated preS-peptides as Novel Therapeutic Concepts for Acute and Chronic Hepatitis B, Global Antiviral Journal, USA, HEP DART 2005, Abstract 023, c. 27.

\* cited by examiner

Figure 1
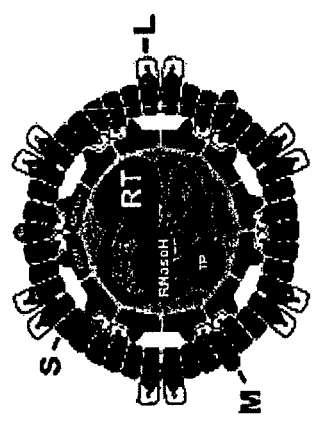
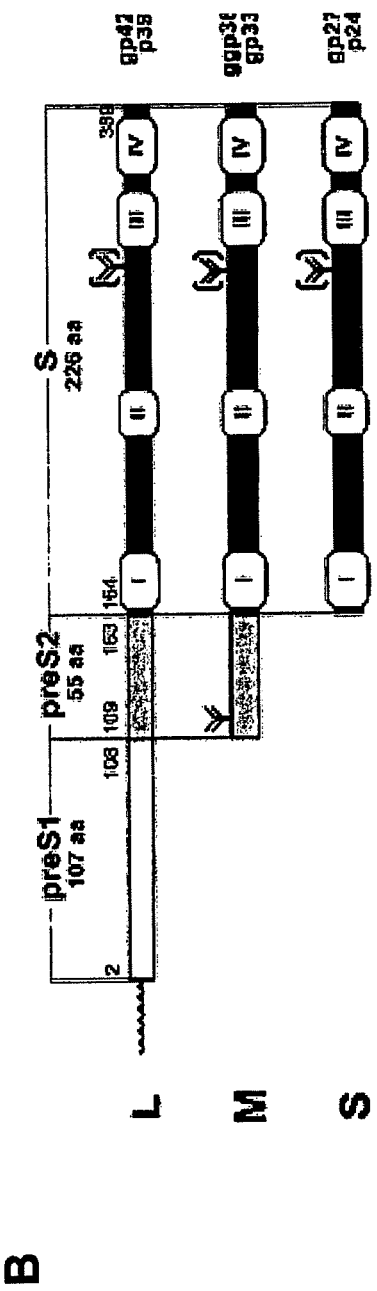

Figure 12
Myrcludex B refers to HBVpreS/2-48(C), wherein (C) refers to HBV genotype C Q46K.

HYDROPHOBIC MODIFIED PRES-DERIVED PEPTIDES OF HEPATITIS B VIRUS (HBV) AND THEIR USE AS HBV AND HDV ENTRY INHIBITORS

This application is a U.S. National Stage of International Application No. PCT/EP2009/000476, filed Jan. 26, 2009, which claims priority to PCT/EP2008/000591, filed Jan. 25, 2008.

The present invention relates to hydrophobic modified preS-derived peptides of hepatitis B virus (HBV) which are derived from a HBV preS consensus sequence and are N-terminal preferably acylated and optional C-terminal modified. These hydrophobic modified preS-derived peptides of HBV are very effective HBV entry inhibitors as well as HDV entry inhibitors and are, thus, suitable for the inhibition of HBV and/or HDV infection, prevention of primary HBV and/or HDV infection as well as treatment of (chronic) hepatitis B and/or D. The present invention further relates to pharmaceutical and vaccine compositions comprising these hydrophobic modified preS-derived peptides of HBV.

BACKGROUND OF THE INVENTION

Today, about 2 billion people carry serological markers of HBV. About 400 million of them are chronically infected with HBV. According to the center of disease control (CDC) 15-25% of chronically HBV infected people are prone to develop hepatocellular carcinoma (HCC) within a decade if they do not receive appropriate treatment (1). HBV-related HCC has a poor prognosis and HBV has therefore been classified by the world health organization (WHO) as the most important naturally occurring human carcinogen. Despite the existence of a prophylactic vaccine, the number of infections will rise in the upcoming decades due to the increasing world population and the limitation of prophylaxis in the poor countries.

In industrial countries HBV is primarily transmitted via the parenteral route. 90-95% of the acutely infected, immuno competent individuals clear the virus, thereby gaining life long immune protection. About 5-10% of them develop chronic Hepatitis B (300,000-500,000 persons in Germany). In contrast, in high endemic areas, particularly Central Africa and Eastern Asia, the main mode of transmission is vertically from mother to child. Unfortunately, infection of not fully immunocompetent children results in a 90-98% chronic course of the disease. Hepatitis B-related HCC is therefore the most common malignancy in many of these countries.

Currently approved therapeutic regiments for the treatment of chronic hepatitis B virus (HBV) infections either address replication steps of the viral genome after an already established infection (Lamivudine, Adefovir, Entecavir) or act as modulators of the immune system (interferon alpha). Unfortunately, only 10-25% of the patients preserve a sustained virological response upon such therapies, reflecting—inter alia—the fast selection of nucleo(s)tide resistant mutants. Despite the availability of a preventative vaccine, it is therefore of utmost importance to develop novel therapeutics that target so far unaffected replication steps e.g. virus entry.

Specific inhibition of virus entry is an attractive therapeutic concept to control and eventually eliminate acute and chronic infections. For HIV, interference with virus entry has been successfully accomplished by a gp41 protein-derived peptide consisting of 36 amino acids (Fuzeon®) which prevents fusion of the viral and the cellular membrane (2).

Despite of the availability of a prophylactic vaccine and reverse transcriptase (RT) inhibitors, the number of HBV-infected people and the number of HBV-related deaths worldwide (presently about 500,000 per year) is increasing. About two thirds of primary liver cancers are attributable to persistent HBV infection (3).

Current treatment pursues two strategies: (i) interferon (IFN alpha) treatment modulates immune responses against HBV and displays a direct antiviral effect, which leads to long-term clinical benefit in about 30% of treated patients without eradication of the virus; (ii) administration of viral reverse transcriptase inhibitors suppresses viral replication and is accompanied by significant biochemical and histological improvements after one year of treatment. However, long-term treatment is associated with the emergence of resistant virus strains (4).

HBV is the prototype of a family of small, enveloped DNA viruses of mammals and birds (5). The HBV envelope encloses three proteins termed L-(large), M-(middle) and S-(small) (see FIG. 1A). They share the C-terminal S-domain with four transmembrane regions. The M- and L-protein carry additional N-terminal extensions of 55 (preS2) and, genotype-dependent, 107 or 118 aa (preS1) (see FIG. 1B). In virions the stoichiometric ratio of L, M and S is about 1:1:4, while the more abundantly secreted non-infectious subviral particles (SVPs) contain almost exclusively S- and only traces of L-protein (6). During synthesis, the preS1-domain of L is myristoylated and translocated through the ER. This modification is essential for HBV infectivity (7, 8).

Studies of the early events of HBV infection have been limited, since neither cell culture systems nor small animal models were available until recently (9). The development of the HBV susceptible cell line HepaRG facilitated systematic investigations of HBV entry and resulted in the discovery of envelope protein-derived entry inhibitors (10).

Furthermore, to date there exists no effective therapy for HDV infection, a satellite virusoid utilizing HBV envelope proteins for the entry into hepatocytes (15, 17, 20). There is a need in the art to provide effective therapies against HDV infection.

Thus, the present invention aims to improve the methods and means for the inhibition, prevention and/or treatment of HBV infection and other HBV-related diseases as present in the prior art and it is, thus, an objective of the present invention to provide improved methods and means which allow for a targeted and effective inhibition, prevention and/or treatment of HBV infection and HBV-related diseases.

It is a further objective of the present invention to provide methods and means for the inhibition, prevention and/or treatment of HDV infection and HDV-related diseases.

SUMMARY OF THE INVENTION

According to the present invention this object is solved by providing hydrophobic modified preS-derived peptides of HBV.

Said hydrophobic modified preS-derived peptides have the general formula $$H_m - P - R_n,$$

P is said preS-derived peptide and comprises the amino acid sequence of the HBV preS consensus sequence or variants thereof.

H is said hydrophobic modification of the preS-derived peptide P, which is N-terminal of P and selected from acylation and addition of hydrophobic moieties; wherein m is at least 1.

R is an optional C-terminal modification (i.e. n is 0 or at least 1) of said preS-derived peptide P.

According to the present invention this object is furthermore solved by providing a pharmaceutical composition comprising at least one hydrophobic modified preS-derived peptide of HBV as defined herein and optionally a pharmaceutically acceptable carrier and/or excipient.

According to the present invention this object is furthermore solved by providing the hydrophobic modified preS-derived peptide(s) of HBV and/or respective pharmaceutical composition(s) of the invention for the diagnosis, prevention and/or treatment of diseases.

According to the present invention this object is furthermore solved by providing the hydrophobic modified preS-derived peptide(s) of HBV or the pharmaceutical composition(s) of the invention for the inhibition of HBV and/or HDV infection; for the prevention of a primary HBV and/or HDV infection and/or for the treatment of hepatitis B and/or D.

According to the present invention this object is furthermore solved by using the hydrophobic modified preS-derived peptide(s) of HBV or the pharmaceutical composition(s) of the invention for the manufacture of a medicament for the inhibition of HBV and/or HDV infection; for the prevention of a primary HBV and/or HDV infection and/or for the treatment of (chronic) hepatitis B and/or D.

According to the present invention this object is furthermore solved by methods of inhibiting of HBV and/or HDV infection; of preventing a primary HBV and/or HDV infection and/or treating (chronic) hepatitis B and/or D by utilizing the hydrophobic modified preS-derived peptide(s) of HBV or the pharmaceutical composition(s) of the invention.

According to the present invention this object is furthermore solved by providing a vaccine composition comprising at least one hydrophobic modified preS-derived peptide of HBV as defined herein and optionally a pharmaceutically acceptable carrier and/or excipient.

DESCRIPTION OF THE PREFERRED EMBODIMENTS OF THE INVENTION

Before the present invention is described in more detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art. For the purpose of the present invention, all references cited herein are incorporated by reference in their entireties.

Hydrophobic Modified preS-Derived Peptides of HBV

As outlined above, the present invention provides hydrophobic modified preS-derived peptides of hepatitis B virus (HBV).

The envelope of HBV encloses three proteins termed L (large), M (middle) and S (small) (see FIG. 1A). They share the C-terminal S-domain with four transmembrane regions. The M- and L-protein carry additional N-terminal extensions of 55 and, genotype-dependent, 107 or 118 amino acids (preS2- and preS1) (see FIG. 1B).

Thus, the expression "preS-derived" peptide of HBV according to the present invention refers to a peptide with an amino acid sequence that corresponds to the N-terminal extensions of the L-protein of HBV, preS1, preferably to a consensus sequence of the species and genotypes A to H as well as of woolly monkey (WMHBV), chimpanzee and gorilla hepatitis B viruses, but it also refers to variants thereof, preferably N-terminally and/or C-terminally truncated variants, amino acid substitution variants.

SEQ ID NO. 1 shows the HBV preS consensus amino acid sequence of the species and genotypes A to H as well as of woolly monkey (WMHBV).

See the alignment in FIG. 2 showing the HBV preS consensus sequence (Consensus) and the eight HBV genotypes (A-H) as well as the woolly monkey HBV (WMHBV) preS sequence encompassing amino acids 2-48. Note that the genotypes A, B, C, E, F, G and H have up to eleven additional amino acids at their N-termini.

The amino acid sequence of HBV "genotype C" within this application refers to an artificial sequence, which corresponds to or is identical to the HBV Genotype C, as e.g. shown in Genbank ABV02850.1, except that position 46 (according to the numbering as described below) is Lys (K) in the genotype C of the present invention instead of Gln (Q) as in the Genbank sequence; the HBV genotype C sequence of this application can also be referred to as "HBV genotype C Q46K". See also SEQ ID NOs. 4, 12, 21-27.

FIG. 2 also shows the numbering of the amino acid residues of the HBV preS consensus sequence, which will be referred to throughout this specification:

Amino acid residue number 1 is the methionine (Met1) of genotype D (formerly described as subtype ayw, see also SEQ ID NO. 5), whereas amino acid residue number (−11) is the methionine (Met(−11)) of genotype C (SEQ ID NO. 4). In vivo Met1 or Met(−11), respectively, is cleaved off by a cellular methionyl aminopeptidase and modified by a subsequent transfer of a myristoyl residue from Myristoyl-CoA to amino acid residue number 2 glycine (Gly2) or amino acid residue number (−10) glycine (Gly(−10)), respectively, by N-myristoyl transferase. The N-terminal amino acid residue of genotype D is the natural amino acid Glycin (Gly2) and is numbered 2 according to the respective numbering from the codons of the underlying open reading frame of L (or e.g. Gly(−10) for genotype C).

The HBV preS consensus sequence also comprises the additional N-terminal amino acids of genotypes A, B, C, E, F, G and H (designated at "−" positions). Thus, in total the HBV preS consensus sequence encompasses positions (−11) to 48.

Thus, there is a difference between the above described numbering and the actual listing of amino acids in SEQ ID NO. 1, e.g.

Met (−11), residue number (−11), is listed as amino acid residue 1 in SEQ ID NO. 1;

Gly (−10), residue number (−10), is listed as amino acid residue 2 in SEQ ID NO. 1;

Met 1, residue number 1, is listed as amino acid residue 12 in SEQ ID NO. 1;

Gly 2, residue number 2, is listed as amino acid residue 13 in SEQ ID NO. 1;

Gly 48, residue number 48, is listed as amino acid residue 58 in SEQ ID NO. 1.

```
HBV preS consensus sequence
(positions (-11) to 48)
                                         SEQ ID NO: 1
(-11)-M GGWSS TPRKG MGTNL SVPNP LGFFP DHQLD PAFRA
NSNNP DWDFN PNKDH WPEAN KVG-48

HBV Genotype A
                                         SEQ ID NO: 2
(-11)-M GGWSS KPRKG MGTNL SVPNP LGFFP DHQLD PAFGA
NSNNP DWDFN PVKDD WPAAN QVG-48

HBV Genotype B
                                         SEQ ID NO: 3
(-11)-M GGWSS KPRKG MGTNL SVPNP LGFFP DHQLD PAFKA
NSENP DWDLN PHKDN WPDAN KVG-48 artificial amino acid sequence, which corresponds
to HBV Genotype C except that position 46 is
Lys (K) instead of Gln (Q); Q46K
                                         SEQ ID NO: 4
(-11)-M GGWSS KPRQG MGTNL SVPNP LGFFP DHQLD PAFGA
NSNNP DWDFN PNKDH WPEAN KVG-48

HBV Genotype D
                                         SEQ ID NO: 5
1-MGQNL STSNP LGFFP DHQLD PAFRA NTANP DWDFN PNKDT
WPDAN KVG-48

HBV Genotype E
                                         SEQ ID NO: 6
(-10)-MGLSW TVPLE WGKNI STTNP LGFFP DHQLD PAFRA
NTRNP DWDHN PNKDH WTEAN KVG-48

HBV Genotype F
                                         SEQ ID NO: 7
(-11)-M GAPLS TTRRG MGQNL SVPNP LGFFP DHQLD PLFRA
NSSSP DWDFN TNKDS WPMAN KVG-48

HBV Genotype G
                                         SEQ ID NO: 8
(-10)-MGLSW TVPLE WGKNL SASNP LGFLP DHQLD PAFRA
NTNNP DWDFN PKKDP WPEAN KVG-48

HBV Genotype H
                                         SEQ ID NO: 9
(-11)-M GAPLS TARRG MGQNL SVPNP LGFFP DHQLD PLFRA
NSSSP DWDFN TNKDN WPMAN KVG-48

WMHBV
                                         SEQ ID NO: 10
1-MGLNQ STFNP LGFFP SHQLD PLFKA NAGSA DWDKN PNKDP
WPQAH DTA-48
```

For SEQ ID NOs. 2-10 see also Genbank Accession numbers:

| | |
|---|---|
| HBV Genotype A | Genbank AAT28684.1 |
| HBV Genotype B | Genbank AAU01950.1 |
| HBV Genotype C | Genbank ABV02850.1 (wherein position 46 is Lys (K) (as in SEQ ID NO. 4) instead of Gln (Q) (of ABV02850.1) |
| HBV Genotype D | Genbank AAR19337.1 |
| HBV Genotype E | Genbank ABS31101.1 |
| HBV Genotype F | Genbank ABK19774.1 |
| HBV Genotype G | Genbank AAF34735.1/AF160501_3 |
| HBV Genotype H | Genbank AAM09052.1 |
| WMHBV | Genbank AAC16905.1 |

A hydrophobic modified preS-derived peptide of HBV according to the present invention has the formula $$H_m\text{—}P\text{—}R_n,$$

wherein
P is said preS-derived peptide;
H is said hydrophobic modification of P;
R is a C-terminal modification of P;
m is at least 1;
n is 0 or at least 1.

The preS-derived peptide of HBV, P, according to the present invention comprises:
the amino acid sequence of the HBV preS consensus sequence as shown in SEQ ID NO. 1 or
variants thereof.

"Variants" are preferably N-terminally and/or C-terminally truncated variants, amino acid substitution or deletion variants, or prolonged variants. Variants comprise furthermore an amino acid sequence comprising modified amino acid(s), unnatural amino acid(s) or peptidomimetic(s) or further compounds which can mimic a peptide backbone/structure.

Preferably, variants are selected from N-terminally and/or C-terminally truncated variants of of SEQ ID NO. 1; amino acid substitution or deletion variants; variants comprising modified amino acid(s), unnatural amino acid(s) or peptidomimetic(s) or further compounds which can mimic a peptide backbone/structure.

According to the invention, a variant of a hydrophobic modified preS-derived peptide contains at least 10 or 20 consecutive amino acids of SEQ ID NO. 1 and can consist of 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or more amino acids of SEQ ID NO. 1 or its variants.

N-terminally and/or C-terminally truncated variants comprise preferably at least 48 consecutive amino acids of SEQ ID NO. 1 (preferably residues 2 to 48), more preferably at least 17 consecutive amino acids of SEQ ID NO. 1 (preferably residues 5 to 21) or at least 20 consecutive amino acids of SEQ ID NO. 1 (preferably residues 2 to 21).

The term "variant" also refers to the homologous sequences found in the different viral species, strains or subtypes of the hepadnavirus genus, such as HBV strain alpha1, HBV strain LSH (chimpanzee isolate), woolly monkey HBV (WMHBV), or strains selected from the group consisting of the HBV genotypes A to H, as well as the HBV genotype C as defined herein, Q46K (such as SEQ ID NO. 4).

The term "variant" also refers to homologous sequences which show at least 50% sequence identity to SEQ ID NO. 1 or any other amino acid sequence disclosed herein, preferably 70%, more preferably 80%, even more preferably 90% or 95%.

Thus, in preferred hydrophobic modified preS-derived peptide according to the invention P comprises a variant of SEQ ID NO. 1 with an amino acid sequence of the different viral species, strains or subtypes, preferably of the genotypes of HBV or woolly monkey HBV (WMHBV) or variants thereof.

Preferably, P comprises an amino acid sequence selected from SEQ ID NOs. 2 to 10 or variants thereof (see also FIG. 2).

In a preferred embodiment in the hydrophobic modified preS-derived peptides according to the invention P comprises a variant of SEQ ID NO. 1 with an amino acid sequence selected from
amino acid residues 2 to 21,
amino acid residues 5 to 21,
amino acid residues 5 to 15 or
amino acid residues 9 to 15 (see also [SEQ ID NO. 15])

of the HBV preS consensus sequence as shown in SEQ ID NO. 1.

More preferably, P does not comprise amino acid substitutions and/or deletions at residues 9 to 22 of SEQ ID NO. 1, such as by deleting residues 17 to 21.

More preferably, P does not comprise amino acid substitutions and/or deletions at residues 9 to 15 of SEQ ID NO. 1.

More preferably, the sequence motif NPLGFFP [SEQ ID NO. 15] (corresponding to residues 9 to 15 of SEQ ID NO. 1) is not interrupted or modified, such as by replacing residues 11-15 by D-amino acids.

More preferably, in the hydrophobic modified preS-derived peptides according to the invention P comprises a variant of SEQ ID NO. 1 with an amino acid sequence selected from
  amino acid residues 2 to 48 of the consensus sequence [SEQ ID NO. 11];
  amino acid residues 2 to 48 of genotype C [SEQ ID NO. 12];
  amino acid residues 2 to 21 of genotype C [SEQ ID NO. 13];
  amino acid residues 5 to 21 of genotype C [SEQ ID NO. 14];
  amino acid residues 9 to 15 of genotype C [SEQ ID NO. 15];
  amino acid residues 2 to 48 of genotype D [SEQ ID NO. 16];
  amino acid residues 5 to 48 of genotype D [SEQ ID NO. 17];
  amino acid residues 2 to 33 of genotype D [SEQ ID NO. 18]
  amino acid residues 5 to 33 of genotype D [SEQ ID NO. 19]
  amino acid residues 2 to 21 of genotype D [SEQ ID NO. 20];
  amino acid residues 9 to 15 of genotype D [SEQ ID NO. 15].

Thus preferably, P comprises an amino acid sequence selected from SEQ ID NOs. 11 to 20 or variants thereof.

For preferred amino acid sequences of P see also below, Tables 1-7, Figures and Examples.

"Variants" of SEQ ID NO. 1 also comprise variants or "analogues" comprising amino acid deletions, amino acid substitutions, such as conservative or non conservative replacement by other amino acids or by isosteres (modified amino acids that bear close structural and spatial similarity to protein amino acids), amino acid additions or isostere additions, as long as the sequences elicit 70% inhibition of HBV infection with a peptide concentration below 10 µM, and preferably below 1 µM.

Conservative amino acid substitutions typically relate to substitutions among amino acids of the same class. These classes include, for example,
  amino acids having uncharged polar side chains, such as asparagine, glutamine, serine, threonine and tyrosine;
  amino acids having basic side chains, such as lysine, arginine, and histidine;
  amino acids having acidic side chains, such as aspartic acid and glutamic acid; and
  amino acids having nonpolar side chains, such as glycine, alanine, valine, leucine, isoleucine, proline, phenylalanine, methionine, tryptophan, and cysteine.

The hydrophobic modified preS-derived peptides of the invention can preferably be modified to have increased immunogenic properties. Such increased immunogenic properties refer for instance to increasing the range of antibodies elicited following immunization, or to allowing the production of antibodies capable of neutralizing infection by various viral strains.

In another embodiment, the hydrophobic modified preS-derived peptides of the invention can preferably be modified to decrease their immunogenic properties. Such hydrophobic modified preS-derived peptides would be particularly useful in a therapeutical application to inhibit in vivo HBV infection while avoiding or limiting adverse effects.

Thus, preferred sequence motifs to be modified by substitution and/or deletion are sequences responsible for the immunogenicity, such as B-cell epitopes and/or T-cell epitopes, and furthermore antibody recognition motifs.

B-cell epitopes of HBV are preferably amino acid residues 20 to 23, motif DPAF (SEQ ID NO:29), of SEQ ID NO. 1 and amino acid residues 26 to 32, motif NSNNPDW (SEQ ID NO:30) of the consensus sequence (SEQ ID NO. 1) and genotype C (SEQ ID NO. 4) or NTANPDW (SEQ ID NO:31) of genotype D (SEQ ID NO. 5).

In a preferred embodiment amino acid residues 20 to 23 of SEQ ID NO. 1 are modified, preferably by amino acid substitution, and/or the amino acid residues 26 to 32 are modified, preferably by amino acid substitution and/or deletion.

Preferably, amino acid residues 20 to 23 of SEQ ID NO. 1 (motif DPAF; SEQ ID NO:29) are modified by alanine amino acid substitution, preferably into motif APAF (SEQ ID NO:32).

Preferably, amino acid residues 26 to 32 of SEQ ID NO. 1 are modified by alanine amino acid substitution, preferably into motif NANAPDW (SEQ ID NO:33) or NAAAPDW (SEQ ID NO:34).

In a preferred embodiment P comprises an amino acid sequence selected from SEQ ID NOs. 21 to 28 or variants thereof.

See also below, Tables 2, 7 and the respective Figures and Examples.

In a more preferred embodiment P comprises an amino acid sequence selected from
  SEQ ID NO. 11 (residues 2 to 48 of the consensus sequence),
  SEQ ID NO. 12 (residues 2 to 48 of genotype C),
  SEQ ID NO. 13 (residues 2 to 21 of genotype C),
  SEQ ID NO. 4 (residues −11) to 48 of genotype C), and
  SEQ ID NO. 20 (residues 2 to 21 of genotype D).

The hydrophobic modification (H) of the preS-derived peptide P is N-terminal of P.

"N-terminal" refers to the hydrophobic modification at the N-terminus, i.e. the respective first amino acid residue (e.g. Gly 2), but comprises also the hydrophobic modification in close proximity to the N-terminus, such as respective amino acid residues (−4), (−3), (−2), (−1), 1, 2 or 3 or 4. Thus, the hydrophobic modification can furthermore be obtained by an attachment of a hydrophobic moiety at a site close to the N-terminus of P.

The hydrophobic modification of said preS-derived peptide of HBV according to the present invention adds a hydrophobic moiety to the peptide.

Furthermore, m is at least 1, i.e. modification with at least one hydrophobic moiety or group.

In preferred embodiments of this invention m is 1, 2, 3, 4 or more. That is, P can be modified with more than one hydrophobic moiety or group, such as 2. The hydrophobic moieties or groups can be the same or different to each other.

The hydrophobic modification of said preS-derived peptide of HBV according to the present invention is selected from:

acylation;
addition of hydrophobic moieties.

Acylation is preferably selected from acylation with carboxylic acids, fatty acids, amino acids with lipophilic side chains.

Preferred fatty acids are saturated or unsaturated fatty acids, branched or unbranched fatty acids, preferably with 8 to 22 carbon atoms (C8 to C22).

More preferably, the hydrophobic modification by acylation is selected from acylation with myristoyl (C14), palmitoyl (C16) or stearoyl (C18).

The addition of hydrophobic moieties is preferably selected from addition of cholesterol, derivatives of cholesterol, phospholipids, glycolipids, glycerol esters, steroids, ceramids, isoprene derivatives, adamantane, farnesol, aliphatic groups, polyaromatic compounds.

The attachment of the hydrophobic moieties is preferably by covalent binding, which can be achieved via carbamate, amide, ether, disulfide or any other linkage that is within the skill of the person skilled in the art.

Thus, the hydrophobic modified, preferably acylated preS-derived peptides of this invention are preferably lipopeptides due to their N-terminal lipophilic or hydrophobic group/moiety.

For preferred hydrophobic modified preS-derived peptides, see also Tables 1 and 2.

More preferred hydrophobic modified preS-derived peptides of the invention are the following:
P comprises an amino acid sequence selected from SEQ ID NO. 11, SEQ ID NO. 12, SEQ ID NO. 13, SEQ ID NO. 4, and SEQ ID NO. 20 and
H is a hydrophobic modification by acylation with myristoyl (C14) or stearoyl (C18), preferably stearoyl (C18).

Thus, the more preferred hydrophobic modified preS-derived peptides of the invention are:

| Designation of peptide | Amino acid sequence | Hydrophobic modification |
|---|---|---|
| HBVpreS/2-48$^{stearoyl}$ (consensus) | SEQ ID NO. 11 | Stearoyl (C18) |
| HBVpreS/2-48$^{myr}$ (consensus) | SEQ ID NO. 11 | Myristoyl (C14) |
| HBVpreS/2-48$^{stearoyl}$ (C) | SEQ ID NO. 12 | Stearoyl (C18) |
| HBVpreS/2-48$^{myr}$ (C) | SEQ ID NO. 12 | Myristoyl (C14) |
| HBVpreS/2-21$^{stearoyl}$ (C) | SEQ ID NO. 12 | Stearoyl (C18) |
| HBVpreS/(−11)-48$^{stearoyl}$ (C) | SEQ ID NO. 4 | Stearoyl (C18) |
| HBVpreS/(−11)-48$^{myr}$ (C) | SEQ ID NO. 4 | Myristoyl (C14) |
| HBVpreS/2-21$^{stearoyl}$ (D) | SEQ ID NO. 20 | Stearoyl (C18) |

Wherein (C) refers to HBV genotype C Q46K.

Preferred Embodiment of Genotype C Sequences

In a very preferred embodiment of this invention the hydrophobic modified preS-peptides according to the invention P comprises an amino acid sequence derived from genotype C.

The hydrophobic modified preS-derived peptide(s) of the present invention derived from genotype C inhibit HBV infection more potently than those of the corresponding genotype D. See also FIG. 3 and Table 3.

As discussed above, the amino acid sequence of HBV "genotype C" within this application refers to an artificial sequence, which corresponds to or is identical to the HBV Genotype C, as e.g. shown in Genbank ABV02850.1, except that position 46 (according to the numbering as described below) is Lys (K) in the genotype C of the present invention instead of Gln (Q) as in the Genbank sequence; the HBV genotype C sequence of this application can also be referred to as "HBV genotype C Q46K". See also SEQ ID NOs. 4, 12, 21-27.

The same numbering as described above for the HBV preS consensus sequence is used for the numbering of the amino acid residues of the genotype C sequences (see also FIG. 2), e.g.
Met (−11), residue number (−11), is listed as amino acid residue 1 in SEQ ID NO. 4;
Gly (−10), residue number (−10), is listed as amino acid residue 2 in SEQ ID NO. 4;
Met 1, residue number 1, is listed as amino acid residue 12 in SEQ ID NO. 4;
Gly 2, residue number 2, is listed as amino acid residue 13 in SEQ ID NO. 4 and is listed as amino acid residue 1 in SEQ ID NO. 12;
Gly 48, residue number 48, is listed as amino acid residue 58 in SEQ ID NO. 4 and is listed as amino acid residue 47 in SEQ ID NO. 12.

SEQ ID NO: 12 amino acid sequence, which corresponds to positions 2 to 48 of HBV Genotype C except that position 46 is Lys (K) instead of Gln (Q); Q46K
2-GTNL SVPNP LGFFP DHQLD PAFGA NSNNP DWDFN PNKDH WPEAN KVG-48

P can be preferably selected from
SEQ ID NO. 12 (residues 2 to 48 of genotype C),
SEQ ID NO. 4 (residues (−11) to 48 of genotype C),
SEQ ID NO. 13 (residues 2 to 21 of genotype C),
SEQ ID NO. 14 (residues 5 to 21 of genotype C) and
SEQ ID NO. 15 (residues 9 to 15 of genotype C).

In the preferred embodiment of genotype C sequences a hydrophobic modified preS-derived peptide of hepatitis B virus (HBV) is of the formula

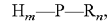

$$H_m\text{—}P\text{—}R_n,$$

wherein preferably
P is a preS-derived peptide comprising the amino acid sequence of SEQ ID NO:12 or a N- or/and C-terminally truncated variant of this sequence of at least 10 consecutive amino acids, or a derivative thereof comprising modified amino acid(s), unnatural amino acid(s) or peptidomimetic(s);
H is a hydrophobic modification of the preS-derived peptide P, which is N-terminal of P and is selected from acylation and addition of hydrophobic moieties;
R is a C-terminal modification of said preS-derived peptide P;
m is at least 1; and
n is 0 or at least 1.

The preferred peptide of the invention is particularly effective for the inhibition of HBV and/or HDV infection, for the prevention of a acute HBV and/or HDV infection and/or for the treatment of hepatitis B and/or D.

Preferably, P comprises or consists of the amino acid sequence of SEQ ID NO. 12 (residues 2 to 48 of genotype C).

Also preferably, P comprises a variant of the amino acid sequence of SEQ ID NO. 12, wherein a variant contains at least 10 consecutive amino acid residues of SEQ ID NO. 12 (preferably residues 9 to 18), more preferably 15 or 20, and can consist of 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or more amino acid residues of SEQ ID NO. 12.

Preferably, the consecutive amino acid residues of SEQ ID NO. 12 that are contained in P are selected from
amino acid residues 9 to 15 of genotype C [=SEQ ID NO. 15],
amino acid residues 2 to 15 of genotype C,
amino acid residues 9 to 18 of genotype C, amino acid residues 2 to 18 of genotype C,
amino acid residues 2 to 20 of genotype C,
amino acid residues 2 to 21 of genotype C [=SEQ ID NO. 13],
amino acid residues 5 to 21 of genotype C [=SEQ ID NO. 14],
amino acid residues 2 to 25 of genotype C,
amino acid residues 2 to 30 of genotype C,
amino acid residues 2 to 35 of genotype C,
amino acid residues 2 to 40 of genotype C,
amino acid residues 2 to 45 of genotype C,
amino acid residues 2 to 46 of genotype C, or
amino acid residues 2 to 48 of genotype C [=SEQ ID NO. 12].

In an embodiments, P contains the respective remaining amino acid residues of SEQ ID NO. 12, namely
amino acid residues 16 to 48 of genotype C,
amino acid residues 19 to 48 of genotype C,
amino acid residues 21 to 48 of genotype C,
amino acid residues 22 to 48 of genotype C,
amino acid residues 26 to 48 of genotype C,
amino acid residues 31 to 48 of genotype C,
amino acid residues 36 to 48 of genotype C,
amino acid residues 41 to 48 of genotype C,
amino acid residues 46 to 48 of genotype C, or
amino acid residues 47 to 48 of genotype C,
which are either identical to the respective amino acid residues of SEQ ID NO. 12 or are a derivative thereof,
wherein a derivative comprises at least one modification selected from an amino acid substitution, an amino acid deletion, a modified amino acid, an unnatural amino acid or a peptidomimetic,
wherein the at least one modification is 1, 2, 3, 4, 5 or more modifications.

Preferred amino acid substitutions are described herein.

Preferably, P comprises an amino acid sequence selected from
amino acid sequence containing amino acid residues 2 to 15 of SEQ ID NO. 12 and, adjacent thereto a derivative of amino acid residues 16 to 48 of SEQ ID NO. 12;
amino acid sequence containing amino acid residues 2 to 20 of SEQ ID NO. 12 and, adjacent thereto a derivative of amino acid residues 21 to 48 of SEQ ID NO. 12;
amino acid sequence containing amino acid residues 2 to 25 of SEQ ID NO. 12 and, adjacent thereto a derivative of amino acid residues 26 to 48 of SEQ ID NO. 12;
amino acid sequence containing amino acid residues 2 to 30 of SEQ ID NO. 12 and, adjacent thereto a derivative of amino acid residues 31 to 48 of SEQ ID NO. 12;
amino acid sequence containing amino acid residues 2 to 35 of SEQ ID NO. 12 and, adjacent thereto a derivative of amino acid residues 36 to 48 of SEQ ID NO. 12;
amino acid sequence containing amino acid residues 2 to 40 of SEQ ID NO. 12 and, adjacent thereto a derivative of amino acid residues 41 to 48 of SEQ ID NO. 12;
amino acid sequence containing the amino acid sequence of SEQ ID NO. 12;
wherein a derivative comprises at least one modification selected from an amino acid substitution, an amino acid deletion, a modified amino acid, an unnatural amino acid or a peptidomimetic,
wherein the at least one modification is 1, 2, 3, 4, 5 or more modifications.

In the preferred embodiment of genotype C sequences:
P comprises an amino acid sequence selected from SEQ ID NO. 12 or the respectively described variants/derivatives/modifications, H is a hydrophobic modification by acylation with myristoyl (C14) or stearoyl (C18), preferably myristoyl (C14).

Modification by myristoylation is preferred in in vivo and medicinal applications due to its higher safety, e.g. not the adverse effects of the stearoyl group (innate immune response etc).

Thus, the more preferred hydrophobic modified preS-derived peptides of the invention are:

| Designation of peptide | Amino acid sequence |
|---|---|
| HBVpreS/(−11)-48$^{myr}$ (C) | [SEQ ID NO. 4] |
| HBVpreS/2-48$^{myr}$ (C) | [SEQ ID NO. 12] |
| HBVpreS/2-21$^{myr}$ (C) | [SEQ ID NO. 13] |
| HBVpreS/5-21$^{myr}$ (C) | [SEQ ID NO. 14] |
| HBVpreS/9-15$^{myr}$ (C) | [SEQ ID NO. 15] |
| most preferably | |
| HBVpreS/2-48$^{myr}$ (C) | [SEQ ID NO. 12]. |

The C-terminal modification (R) of said preS-derived peptide P is preferably a modification with a moiety that protects from degradation, such as in vivo degradation.

"C-terminal" refers to the modification at the C-terminus, i.e. the respective last amino acid residue, but comprises also the modification in close proximity to the C-terminus, such as the last but one amino acid residue, the last but two amino acid residue or more amino acid residues (e.g. introduction of one D-amino acid that protects the carrier from enzymatic degradation e.g. by the action of carboxypeptidases).

The skilled artisan will be able to select the respective suitable moiety(s) depending on the respective application.

Preferred moieties that protect from degradation are selected from amides, D-amino acids, modified amino acids, cyclic amino acids; natural and synthetic polymers, such as PEG, glycane.

In an embodiment P is fused to a peptide or protein, preferably selected from albumin, Fc domains of human IgGs.

The fusion is preferably C-terminal of P.

Furthermore, n is 0 or at least 1, i.e. the C-terminal modification (R) is optional.

Preferably, n is 1.

In further embodiments of this invention n is 1, 2, 3, 4 or more. That is, the C-terminus of P or its proximity can be modified with more than one moiety or group, such as 2. The moieties or groups can be the same or different to each other.

In an embodiment of this invention H and/or R are linked to P via a linker or spacer.

Linker or spacer are known to the skilled artisan, such as polyalanine, polyglycin, carbohydrates, $(CH_2)_n$ groups.

The skilled artisan will, thus, be able to select the respective suitable linker(s) or spacer(s) depending on the respective application.

In a preferred embodiment, the hydrophobic modified preS-derived peptide according to the invention carry a label or a tag, preferably selected from a fluorescent dye, a radioisotope and a contrast agent.

Preferred radioisotopes are $^{131}$I, $^{125}$I, $^{99m}$Tc, $^{18}$F, $^{68}$Ga, $^{111}$In, $^{90}$Y, $^{177}$Lu.

Preferred fluorescent dyes are Alexa dyes, derivatives of rhodamine and fluorescein, Cy-dyes.

Preferred contrast agents are Gadolinium (Gd) complexes, supramagnetic iron (Fe) complexes and particles, compounds containing atoms of high atomic number, i.e. iodine for computer tomography (CT), microbubbles and carriers such as liposomes that contain these contrast agents.

The peptides of this invention can be prepared by a variety of procedures readily known to those skilled in the art, in general by synthetic chemical procedures and/or genetic engineering procedures.

Synthetic chemical procedures include more particularly the solid phase sequential and block synthesis (11). The solid phase sequential procedure can be performed using established automated methods such as by use of an automated peptide synthesizer. In this procedure an a-amino protected amino acid is bound to a resin support. The resin support employed can be any suitable resin conventionally employed in the art for the solid phase preparation of (poly)peptides, preferably polystyrene which has been copolymerized with polyoxyethylen to provide sites for ester formation with the initially introduced o-amino protected amino acid. This optimized method, applied by the inventors, has been explicitly described (see e.g. 12). The amino acids are introduced one by one (step-wise). Each synthesis cycle corresponding to the introduction of one amino acid includes a deprotection step, successive washing steps, a coupling step with activation of the amino acid, and subsequent washing steps. Each of these steps is followed by a filtration. The reactive agents for coupling are the classical reactive agents for (poly)peptide synthesis such as dicyclohexylcarbodiimide, hydroxybenzotriazole, benzotriazil-1-yl-oxytris(dimethylamino)phosphonium hexafluorophosphate, and diphenylphosphorylazide. After synthesis of the polypeptide on the resin, the polypeptide is separated from the resin by a treatment with a strong acid such as trifluoroacetic acid in the presence of anisol, ethanedithiol or 2-methylindole. The compound is then purified by the classical techniques of purification, in particular by means of HPLC.

The peptides of the present invention may also be obtained by coupling (poly)peptide fragments that are selectively protected, this coupling being effected e.g. in a solution.

The peptides can further be produced by genetic engineering techniques as known to the skilled artisan. An eukaryotic expression system, such as the baculovirus system, is particularly suitable. According to this procedure proteins are expressed in insect cells infected with a recombinant baculovirus containing a nucleic acid sequence encoding a heterologous protein and regulating nucleic acid sequences, such as a promoter. Several cell-lines are available for infection with recombinant baculovirus, such as cell line Sf-9, available from the American Type Culture Collection (CRL 1711). Expression in prokaryotic expression system, such as *E. coli*, is also particularly suitable.

The introduction of the hydrophobic moiety to the peptide can be accomplished by a variety of procedures readily known to those skilled in the art, including synthetic and genetic engineering approaches.

Alternatively, the peptides and/or fusion peptides (i.e. hydrophobic modified peptides) can be produced by stably transfected eukaryotic cell lines, like CHO and other cell lines which are known in the art and usually used for generating vaccines and the like. Due to the intrinsic property that the N-terminal 47-preS1 amino acids promote secretion of a myristoylated protein/peptide, the biologically active hydrophobic modified peptide can be extracted from cell culture supernatants.

Characteristics of the Hydrophobic Modified preS-Derived Peptides of the Invention The hydrophobic modified preS-derived peptides of the present invention are versatile hepatitis virus entry inhibitors and also exhibit a hepatotropism/liver tropism, i.e. they target to the liver. The liver tropism is shown in particular in FIG. 11.

Said hepatotropism is further disclosed in the corresponding US provisional patent application of the inventors with the title: "Hydrophobic modified preS-derived peptides of hepatitis B virus (HBV) and their use as vehicles for the specific delivery of compounds to the liver" which was filed at the same day and which is enclosed herein by reference in its entirety.

The hydrophobic modified preS-derived peptide(s) of HBV of the present invention are very suitable and effective entry inhibitors of HBV, but also of HDV, either in vitro (e.g. by preventing binding and/or internalisation of HBV particles to hepatocytes) or in vivo.

As can be seen from the Figures and Examples, the hydrophobic modified preS-derived peptide(s) of the present invention have a high inhibitory activity, i.e. they effectively inhibit HBV and/or HDV infection at very low doses. The $IC_{50}$ values of the more preferred embodiments are in the range of 0.01 to 500 nM, preferably 0.025 to 50 nM, more preferably 0.05 to 25 nM. See also Table 1.

The hydrophobic modified preS-derived peptide(s) of the present invention derived from genotype C inhibit HBV infection more potently than those of the corresponding genotype D.

Furthermore, the hydrophobic modified preS-derived peptides of the present invention can be tailored to not comprise immunogenic epitopes but still exhibit a strong inhibitory activity, such as HBVpreS/2-21$^{stearoyl}$ which does not comprise the immunogenic epitopes in its sequence but still has a $IC_{50}$ of about 8 nM.

The hydrophobic modified preS-derived peptide(s) of HBV of the invention are also able of cross preventing HBV genotype C and D, because a peptide derived from genotype C (such as HBVpreS/2-21$^{stearoyl}$(C) or HBVpreS/2-48$^{myr}$(C)) can inhibit the entry of HBV genotype D.

Pharmaceutical and Vaccine Compositions

As outlined above, the present invention provides a pharmaceutical composition comprising at least one hydrophobic modified preS-derived peptide of HBV as defined herein and optionally a pharmaceutically acceptable carrier and/or excipient.

The pharmaceutical composition according to the present invention comprises:
 at least one hydrophobic modified preS-derived peptide of HBV as defined herein;
 a conjugate as defined herein;
 and
 optionally a pharmaceutically acceptable carrier and/or excipient.

The pharmaceutical compositions according to the present invention are very well suited for all the uses and methods described herein.

As outlined above, the present invention provides a vaccine composition comprising at least one hydrophobic modified preS-derived peptide of HBV as defined herein and optionally a pharmaceutically acceptable carrier and/or excipient.

The vaccine compositions according to the present invention are very well suited for the uses and methods described herein.

A "pharmaceutically acceptable carrier or excipient" refers to any vehicle wherein or with which the pharmaceutical or vaccine compositions according to the invention may be formulated. It includes a saline solution such as phosphate buffer saline. In general, a diluent or carrier is selected on the basis of the mode and route of administration, and standard pharmaceutical practice.

Medical Applications

As outlined above, the present invention provides the first medical use of the hydrophobic modified preS-derived peptide(s) of HBV and/or respective pharmaceutical composition(s) of this invention.

Thus, the hydrophobic modified preS-derived peptide(s) of HBV or the pharmaceutical composition(s) according to the invention are suitable and, thus, provided for the diagnosis, prevention and/or treatment of diseases.

As outlined above, the present invention further provides the hydrophobic modified preS-derived peptide(s) of HBV and/or respective pharmaceutical composition(s) of this invention for the diagnosis, prevention and/or treatment of certain diseases.

In a preferred embodiment the hydrophobic modified preS-derived peptide(s) of HBV or the pharmaceutical composition(s) of the invention are provided for the inhibition of HBV and/or HDV infection; for the prevention of a primary HBV and/or HDV infection and/or for the treatment of hepatitis B and/or D, preferably chronic hepatitis B and/or D.

In a preferred embodiment the hydrophobic modified preS-derived peptide(s) of HBV or the pharmaceutical composition(s) of the invention are used for the manufacture of a medicament for the inhibition of HBV and/or HDV infection; for the prevention of a primary HBV and/or HDV infection and/or for the treatment of hepatitis B and/or D.

Preferably, the hydrophobic modified preS-derived peptide(s) of HBV or the pharmaceutical composition(s) of the invention are provided for the inhibition of HBV and/or HDV infection.

Preferably, the hydrophobic modified preS-derived peptide(s) of HBV or the pharmaceutical composition(s) of the invention are provided for the prevention of a primary HBV and/or HDV infection.

Preferably, the HBV infection of any genotype of HBV is inhibited or prevented.

The hydrophobic modified preS-derived peptide(s) of HBV of the invention are able of the cross prevention of HBV genotype C and D, because a peptide derived from genotype C (such as HBVpreS/2-21$^{stearoyl}$(C) or HBVpreS/2-48$^{myr}$(C)) can inhibit the entry of HBV genotype D.

In a preferred embodiment the hydrophobic modified preS-derived peptide(s) of HBV or the pharmaceutical composition(s) of the invention are used/provided as HBV and/or HDV entry inhibitors.

Preferably, the hydrophobic modified preS-derived peptide(s) of HBV or the pharmaceutical composition(s) of the invention are provided for the treatment of hepatitis B and/or D, in particular chronic hepatitis B and/or D.

The hydrophobic modified preS-derived peptide(s) of HBV of the present invention are very suitable and effective entry inhibitors of HBV, but also of HDV, either in vitro (e.g. by preventing binding and/or internalisation of HBV particles to hepatocytes) or in vivo.

Furthermore, the invention provides a method of in vitro inhibition of hepatocyte infection by HBV comprising using a hydrophobic modified preS-derived peptide or pharmaceutical composition as described above.

Suitable hepatocytes include human primary hepatocytes or the hepatoma derived cell line called HepaRG (22) (described in the patent application FR 0109044), hepatocytes from *Tupaia belangeri* (23), which are also susceptible to HBV infection.

Furthermore, and as outlined above, the present invention provides methods for inhibiting HBV and/or HDV infection; of preventing a primary HBV and/or HDV infection and/or treating (chronic) hepatitis B and/or D by utilizing the hydrophobic modified preS-derived peptide(s) of HBV or the pharmaceutical composition(s) of the invention.

Route of Administration

Preferably, the route of administration of the hydrophobic modified preS-derived peptides or pharmaceutical compositions of the present invention is selected from subcutaneous, intravenous, oral, nasal, intramuscular, transdermal, inhalative, by suppository.

A preferred embodiment for nasal administration or application is a nasal spray.

Therapeutically Effective Amount

The hydrophobic modified preS-derived peptides or the pharmaceutical compositions of the invention are provided such that they comprise a therapeutically effective amount of said hydrophobic modified preS-derived peptide(s) of said pharmaceutical composition(s).

A "therapeutically effective amount" of a hydrophobic modified preS-derived peptide or a pharmaceutical composition of this invention refers to the amount that is sufficient to inhibit a HBV and/or HDV infection; prevent a primary HBV and/or HDV infection; treat hepatitis B and/or D and/or vaccinate and/or inhibit entry of HBV and/or HDV in vivo.

A preferred therapeutically effective amount is in the range of 10 µg to 1 mg per kg body weight, preferably 10 µg to 100 µg.

For the use of a hydrophobic modified preS-derived peptide of the invention as a vaccine the preferred therapeutically effective amount is in the range of 10 µg to 1 mg per kg body weight.

In case of an IC$_{50}$ value of the hydrophobic modified preS-derived peptide used of about 10 nM, a preferred therapeutically effective amount is about 100 µg per kg body weight or in the range of 1 to 5 mg per patient. The preferred therapeutically effective amount in the range of 1 to 5 mg per patient can be administered once a day or in other embodiments only once every 2-3 days.

The preferred therapeutically effective amount depends on the respective application and desired outcome of inhibition, treatment or vaccination.

The skilled artisan will be able to determine suitable therapeutically effective amounts.

Identification of the HBV Receptor

The invention further relates to a method for in vitro and/or in vivo identification of a hepatocyte receptor involved in the attachment and/or penetration of HBV and/or quantitation of the expression of said receptor that comprises using a hydrophobic modified preS-derived peptide as described above.

Said hepatocyte receptor can be identified in mammals or respective animal models, preferably mouse or human.

In particular, said method comprises the steps comprising:
  contacting a liver biopsy or a hepatocyte with a hydrophobic modified preS-derived peptide of the invention under conditions and for a period of time sufficient to allow specific binding of said peptide to a receptor expressed at the surface of a hepatocyte;
  detecting binding of said peptide to a receptor; and
  identifying said receptor.

This can be achieved according to classical procedures well-known by the skilled in the art. For instance, this could involve radioactive, enzyme or fluorescent labelling of the hydrophobic modified preS-derived peptides of the invention, and subsequent detection with an appropriate method.

A number of fluorescent materials are known and can be utilized as labels. These include, for example, fluorescein, rhodamine, auramine, Texas Red, Cy3, Cy5, DIGE-labels. Enzyme labels comprise conjugation of an enzyme to a molecule of interest, e. g. a polypeptide, and can be detected by any of colorimetric, spectrophotometric, or fluorospectrophotometric techniques.

The inventors identified HBV-preS1-surface protein-derived lipopeptides that efficiently block HBV entry in vitro and in vivo. Biodistribution studies of the present invention on these inhibitory peptides revealed that they selectively accumulate in the liver where they bind to and presumably enter into hepatocytes. This hepatotropism requires N-terminal acylation of the peptide and depends on a certain HBV preS-sequence motif within the N-terminal 47 preS1 amino acids, i.e. within the amino acid residues 2 to 21 (or preferably the minimal sequence of residues 9 to 15). The inventors' observation that this peptide sequence additionally bears a membrane translocation signal which facilitates the transport of even complete fusion proteins across plasma membranes (unpublished results) opens the possibility of specifically delivering any kind of drug to the plasma membrane of hepatocytes or selectively even into this cell.

The inventors have shown that HBV preS1-derived lipopeptides are capable to completely prevent HBV infection in a transplanted uPA-RAG-1 mouse model at very low doses. Pharmakokinetic studies on these HBVpreS-derived entry inhibitors furthermore indicated a remarkable hepatotropism combined with an extraordinary high serum stability ($t_{1/2}$ ca. 60 h) and a long half life time in the target organ ($t_{i/2}$ ca. 24 h). Both N-terminal acylation as well as the integrity of the certain amino acid sequence of the peptides are mandatory. The peptides can, thus, also be used as versatile vectors for liver specific drug targeting to conquer infections of hepatocytes or to treat hepatocellular carcinoma.

(See also corresponding US provisional patent application of the inventors with the title: "Hydrophobic modified preS-derived peptides of hepatitis B virus (HBV) and their use as vehicles for the specific delivery of compounds to the liver", which was filed at the same day).

The inventors have furthermore proven the principle that WMHBV infection can be efficiently blocked through subcutaneous application of HBV envelope protein-derived peptides in vivo. This opens new perspectives for the prevention of acute HBV-infection and therapeutic options for chronic hepatitis B. Since the uPA/RAG-2/Pfp mice used in this invention lack B cells, T cells, and NK cells, a direct inhibitory effect of the peptides on susceptible hepatocytes is assumed. This is supported by the efficient accumulation of acylated preS-derived peptides in the liver, followed by a slow clearance possibly via the biliary route. Both properties permit subcutaneous application at very low doses and low frequencies. Given that 5 injections of 0.2 mg/kg HBV/preS2-48$^{myr}$ within 5 days resulted in the prevention of the establishment of WMHBV infection, continuous administration of the about 30-fold more active peptide HBV/preS2-48$^{stearoyl}$ might be effective at doses below 7 µg/kg≈13 nmol/kg when given daily or every 2 days. Taking into account that the efficient pharmacological dose per body weight obtained in mice has to be corrected for humans (13) by a factor of about 10, the efficient dose per person is expected to be lower than 100 µg/day.

The nucleos(t)ide analogue-based regimen for treatment of chronic HBV infection frequently results in the selection of resistant mutants (4, 14). This demands for alternative strategies and new drugs that address different steps of the HBV replication cycle. Entry inhibition with HBV lipopeptides represents such an approach. Due to the mode of action the inventors assume efficacy against any kind of nucleos (t)ide resistant mutant. Moreover, since the activity of the peptides requires a conserved sequence in the preS1-domain (15), the peptides are active against any HBV-genotype. In contrast to Fuzeon® which targets the HIV gp41 protein thus allowing the emergence of intramolecular compensatory mutations, previous studies indicate that acylated HBV-lipopeptides address a cellular component preventing interaction of HBV with its receptor (16, 17). Therefore, emergence of resistant mutants appears improbable.

Apparent indications for clinical applications of HBVpreS-derived lipopeptides are the prevention of not yet established HBV infections (e.g. post exposure prophylaxis, vertical transmission or prevention of reinfection of the liver transplant). However, entry inhibitors are also effective in chronically infected patients, such as in combination with interferon α or inhibitors of the viral RT. Since maintenance of HBV-chronic infection may depend on a dynamic turnover of infected hepatocytes cleared by the immune system on one hand and (re)infection of cured/naive cells on the other hand (18), it will be interesting to evaluate the efficacy of such therapeutic approaches in the uPA chimeric system to repress spreading of infection and emerging of resistant strains under antiviral treatment (19).

HBVpreS-derived lipopeptides also inhibit in vitro infection of HDV, a satellite virusoid utilizing HBV envelope proteins for the entry into hepatocytes (15, 17, 20). Since to date no effective therapy for HDV infection exists, preS-derived lipopeptides represent the first selective therapy for this often complicated liver disease.

Application of HBVpreS-derived lipopeptides in immune competent patients elicits cellular and humoral immune reactions. This is beneficial for the therapeutic outcome, since it is known that antibodies recognizing epitopes of HBVpreS/2-48 neutralize HBV infection in vitro (21). Moreover, it has been speculated that virus elimination in a natural infection requires the successful establishment of HBVpreS-specific immunity. Thus, in addition to the direct interference with virus entry, stimulation of preS-specific immune responses by the peptide could contribute to virus elimination through cytolytic or non-cytolytic immune reactions, especially in combination with IFNα.

TABLE 1

Preferred hydrophobic modified preS-derived peptides

| Designation of peptide | Amino acid sequence | IC50/IC90 |
| --- | --- | --- |
| HBVpreS/(−11)-48(consensus) | consensus | SEQ ID NO. 1 |
| HBVpreS/2-48$^{myr}$(consensus) | | SEQ ID NO. 11  IC$_{50}$~70 pM |
| HBVpreS/2-48$^{stearoyl}$(consensus) | | SEQ ID NO. 11  IC$_{50}$~50 pM |

TABLE 1-continued

Preferred hydrophobic modified preS-derived peptides

| Designation of peptide | | Amino acid sequence | IC50/IC90 |
|---|---|---|---|
| Genotype C peptides | | | |
| *HBVpreS/(−11)-48$^{myr}$(C) | natural | SEQ ID NO. 4 | IC$_{50}$~4 nM |
| *HBVpreS/(−11)-48$^{stearoyl}$(C) | | SEQ ID NO. 4 | IC$_{50}$~1 nM |
| *HBVpreS/2-48$^{myr}$(C) | | SEQ ID NO. 12 | IC$_{90}$~5 nM |
| *HBVpreS/2-48$^{stearoyl}$(C) | | SEQ ID NO. 12 | IC$_{90}$~1 nM |
| HBVpreS/5-48$^{myr}$(C) | truncated N-terminal | | |
| HBVpreS/5-48$^{stearoyl}$(C) | | | |
| HBVpreS/9-48$^{myr}$(C) | | | |
| HBVpreS/9-48$^{stearoyl}$(C) | | | |
| HBVpreS/2-21$^{myr}$(C) | truncated N- and/or C-terminal | SEQ ID NO. 13 | |
| HBVpreS/2-21$^{stearoyl}$(C) | | SEQ ID NO. 13 | |
| HBVpreS/5-21$^{myr}$(C) | | SEQ ID NO. 14 | |
| HBVpreS/5-21$^{stearoyl}$(C) | | SEQ ID NO. 14 | |
| HBVpreS/9-21$^{myr}$(C) | | | |
| HBVpreS/9-21$^{stearoyl}$(C) | | | |
| HBVpreS/2-15$^{myr}$(C) | | | |
| HBVpreS/2-15$^{stearoyl}$(C) | | | |
| HBVpreS/5-15$^{myr}$(C) | | | |
| HBVpreS/5-15$^{stearoyl}$(C) | | | |
| HBVpreS/9-15$^{myr}$(C)** | | SEQ ID NO. 15 | |
| HBVpreS/9-15$^{stearoyl}$(C)** | | SEQ ID NO. 15 | |
| HBVpreS/(−2)-20$^{palm}$(C) | | | IC$_{50}$~25 nM |
| Genotype D peptides | | | |
| HBVpreS/1-4$^{myr}$(D) | natural | SEQ ID NO. 5 | |
| HBVpreS/2-48$^{myr}$(D) | | SEQ ID NO. 16 | |
| *HBVpreS/2-48$^{stearoyl}$(D) | | SEQ ID NO. 16 | IC$_{90}$~3 nM |
| HBVpreS/5-48$^{myr}$(D) | truncated N-terminal | SEQ ID NO. 17 | |
| *HBVpreS/5-48$^{stearoyl}$(D) | | SEQ ID NO. 17 | IC$_{50}$~4 nM |
| HBVpreS/9-48$^{myr}$(D) | | | |
| *HBVpreS/9-48$^{stearoyl}$(D) | | | IC$_{50}$~1 μM |
| HBVpreS/2-33$^{myr}$(D) | truncated N- and/or C-terminal | SEQ ID NO. 18 | |
| *HBVpreS/2-33$^{stearoyl}$(D) | | SEQ ID NO. 18 | IC$_{50}$~6 nM |
| HBVpreS/2-26$^{myr}$(D) | | | |
| *HBVpreS/2-26$^{stearoyl}$(D) | | | |
| HBVpreS/5-33$^{myr}$(D) | | SEQ ID NO. 19 | |
| *HBVpreS/5-33$^{stearoyl}$(D) | | SEQ ID NO. 19 | IC$_{50}$~7 nM |
| HBVpreS/9-33$^{myr}$(D) | | | |
| *HBVpreS/9-33$^{stearoyl}$(D) | | | IC$_{50}$~500 nM |
| HBVpreS/2-21$^{myr}$(D) | | SEQ ID NO. 20 | |
| *HBVpreS/2-21$^{stearoyl}$(D) | | SEQ ID NO. 20 | IC$_{50}$~2 nM |
| HBVpreS/5-21$^{myr}$(D) | | | |
| HBVpreS/5-21$^{stearoyl}$(D) | | | |
| HBVpreS/9-21$^{myr}$(D) | | | |
| HBVpreS/9-21$^{stearoyl}$(D) | | | |
| HBVpreS/2-15$^{myr}$(D) | | | |
| *HBVpreS/2-15$^{stearoyl}$(D) | | | IC$_{50}$~200 nM |
| HBVpreS/5-15$^{myr}$(D) | | | |
| HBVpreS/5-15$^{stearoyl}$(D) | | | |
| HBVpreS/9-15$^{myr}$(D)** | | SEQ ID NO. 15 | |
| HBVpreS/9-15$^{stearoyl}$(D)** | | SEQ ID NO. 15 | |

$^{myr}$refers to myristoylation of the N-terminus;
$^{palm}$refers to palmitoylation of the N-terminus;
$^{stearoyl}$refers to stearoylation of the N-terminus;
(C)refers to genotype C (with Q46K, as in SEQ ID NO. 4);
(D)refers to genotype D;
*peptides are shown in Figures;
**minimal sequence.

TABLE 2

Preferred hydrophobic modified preS-derived peptides with changes in the immunogenic epitopes

| Designation of peptide | Amino acid sequence |
|---|---|
| HBVpreS/2-48$^{myr}$-Ala$^{21, 23, 29, 30}$(C) | SEQ ID NO. 21 |
| HBVpreS/2-48$^{stearoyl}$-Ala$^{21, 23, 29, 30}$(C) | SEQ ID NO. 21 |
| HBVpreS/(−11)-48$^{myr}$-D20A(C) | SEQ ID NO. 22 |
| HBVpreS/(−11)-48$^{stearoyl}$-D20A(C) | SEQ ID NO. 22 |
| HBVpreS/2-48$^{myr}$-D20A(C) | SEQ ID NO. 23 |
| HBVpreS/2-48$^{stearoyl}$-D20A(C) | SEQ ID NO. 23 |
| HBVpreS/(−11)-48$^{myr}$-SNN(27-29)ANA(C) | SEQ ID NO. 24 |
| HBVpreS/(−11)-48$^{stearoyl}$-SNN(27-29)ANA(C) | SEQ ID NO. 24 |
| HBVpreS/2-48$^{myr}$-SNN(27-29)ANA(C) | SEQ ID NO. 25 |
| HBVpreS/2-48$^{stearoyl}$-SNN(27-29)ANA(C) | SEQ ID NO. 25 |

TABLE 2-continued

Preferred hydrophobic modified preS-derived peptides with changes in the immunogenic epitopes

| Designation of peptide | Amino acid sequence |
|---|---|
| HBVpreS/(−11)-48$^{myr}$-D20A + SNN(27-29)ANA(C) | SEQ ID NO. 26 |
| HBVpreS/(−11)-48$^{stearoyl}$-D20A + SNN(27-29)ANA(C) | SEQ ID NO. 26 |
| HBVpreS/2-48$^{myr}$-D20A + SNN(27-29)ANA(C) | SEQ ID NO. 27 |
| HBVpreS/2-48$^{stearoyl}$-D20A + SNN(27-29)ANA(C) | SEQ ID NO. 27 |
| HBVpreS/2-48$^{myr}$-Ala$^{21, 23, 29, 30}$(D) | SEQ ID NO. 28 |
| *HBVpreS/2-48$^{stearoyl}$-Ala$^{21, 23, 29, 30}$(D) | SEQ ID NO. 28 |

$^{myr}$refers to myristoylation of the N-terminus;
$^{stearoyl}$refers to stearoylation of the N-terminus;
(C)refers to genotype C (with Q46K, as in SEQ ID NO. 4);
(D)refers to genotype D.

TABLE 3

Comparative inhibition studies with hydrophobic modified preS-peptides of genotype C and D

| Designation of peptide | Amino acid sequence | Geno-type | Hydrophobic moiety | Inhibition |
|---|---|---|---|---|
| HBVpreS/2-48$^{myr}$(D) | SEQ ID NO. 16 | D | Myristoyl (C14) | ++ |
| HBVpreS/2-48$^{myr}$(C) | SEQ ID NO. 12 | C | Myristoyl (C14) | +++ |
| HBVpreS/(−11)-48$^{myr}$(C) | SEQ ID NO. 4 | C | Myristoyl (C14) | ++ |
| HBVpreS/2-48$^{stearoyl}$(C) | SEQ ID NO. 12 | C | Stearoyl (C18) | ++++ |
| HBVpreS/(−11)-48$^{stearoyl}$(C) | SEQ ID NO. 4 | C | Stearoyl (C18) | +++ |

See also FIG. 3.
Wherein (C) refers to HBV genotype C Q46K.

TABLE 4

Infection inhibition studies with hydrophobic modified preS-peptides with the consensus sequence.

| Designation of peptide | Amino acid sequence | Hydrophobic moiety | Inhibition |
|---|---|---|---|
| HBVpreS/2-48$^{myr}$(consensus) | SEQ ID NO. 11 | Myristoyl (C14) | ++++ |
| HBVpreS/2-48$^{stearoyl}$(consensus) | SEQ ID NO. 11 | Searoyl (C18) | ++++ |

See also FIG. 4.

TABLE 5

Comparative inhibition studies with C-terminal deletion variants.

| Designation of peptide | Amino acid sequence | Geno-type | Hydrophobic moiety | Inhibition |
|---|---|---|---|---|
| HBVpreS/2-48$^{stearoyl}$(D) | SEQ ID NO. 16 | D | Stearoyl (C18) | +++ |
| HBVpreS/2-33$^{stearoyl}$(D) | SEQ ID NO. 18 | D | Stearoyl (C18) | + |
| HBVpreS/2-26$^{stearoyl}$(D) | | D | Stearoyl (C18) | + |
| HBVpreS/2-21$^{stearoyl}$(D) | SEQ ID NO. 20 | D | Stearoyl (C18) | +++ |
| HBVpreS/2-15$^{stearoyl}$(D) | | D | Stearoyl (C18) | +/− |

See also FIG. 5.

TABLE 6

Comparative inhibition studies with N- and C-terminal deletion variants.

| Designation of peptide | Amino acid sequence | Geno-type | Hydrophobic moiety | Inhibition |
|---|---|---|---|---|
| HBVpreS/2-48$^{stearoyl}$(D) | SEQ ID NO. 16 | D | Stearoyl (C18) | +++ |
| HBVpreS/2-33$^{stearoyl}$(D) | SEQ ID NO. 18 | D | Stearoyl (C18) | + |
| HBVpreS/5-33$^{stearoyl}$(D) | SEQ ID NO. 19 | D | Stearoyl (C18) | + |
| HBVpreS/5-48$^{stearoyl}$(D) | SEQ ID NO. 17 | D | Stearoyl (C18) | + |
| HBVpreS/9-33$^{stearoyl}$(D) | | D | Stearoyl (C18) | +/− |
| HBVpreS/9-48stearoyl | | D | Stearoyl (C18) | +/− |

See also FIG. 6.

TABLE 7

Comparative inhibition studies with hydrophobic modified preS-peptides demonstrating the necessity of amino acid residues 9 to 15 (the minimal sequence)

| Designation of peptide | Amino acid sequence | Geno-type | Inhibition |
|---|---|---|---|
| HBVpreS/2-48$^{stearoyl}$(D) | SEQ ID NO. 16 | D | +++ |
| HBVpreS/2-48$^{stearoyl}$(Δ-AS$^{11-15}$)(D) | | D | − |
| HBVpreS/2-48$^{stearoyl}$(Ala$^{11-15}$)(D) | | D | − |
| HBVpreS/2-48$^{stearoyl}$(Δ17-21)(D) | | D | + |
| HBVpreS/2-48$^{stearoyl}$(Ala$^{17-21}$)(D) | | D | − |
| HBVpreS/2-48$^{stearoyl}$(Ala$^{2-9}$)(D) | | D | − |

See also FIG. 7.

TABLE 8

Comparative inhibition studies with hydrophobic modified preS-peptides

| Designation of peptide | Amino acid sequence | Geno-type | Inhibition |
|---|---|---|---|
| HBVpreS/2-48$^{stearoyl}$(retroinverso)(D) | | D | --- |
| HBVpreS/)2-48$^{stearoyl}$-Ala$^{21, 23, 29, 30}$(D) | SEQ ID NO. 28 | D | ++ | retroinverso amino acid sequence of SEQ ID NO. 16 in the C to N direction
See also FIG. 8.

TABLE 9

Further comparative inhibition studies with hydrophobic modified preS-peptides demonstrating the necessity of amino acid residues 9 to 15 (the minimal sequence)

| Designation of peptide | Amino acid sequence | Geno-type | Inhibition |
|---|---|---|---|
| HBVpreS/2-48$^{stearoyl}$(Ala$^{18}$)(D) | | D | ++ |
| HBVpreS/2-48$^{stearoyl}$(Δ11-15)(D) | | D | --- |
| HBVpreS/2-48$^{stearoyl}$(Ser$^{13}$)(D) | | D | + |
| HBVpreS/2-48$^{stearoyl}$(Arg$^{11}$)(D) | | D | --- |

See also FIG. 9.

The following examples and drawings illustrate the present invention without, however, limiting the same thereto.

BRIEF DESCRIPTION OF THE DRAWINGS

FIG. 1. Schematic representation of the HBV particle and the HBV L-, M- and S-proteins.

(A) The partially double stranded DNA is covalently associated with the viral polymerase complex, consisting of the terminal protein, (TP), the reverse transcriptase (RT) and the RNaseH. The genome is encapsulated by an icosahedral shell, built of 120 core-protein dimers. The 3 HBV surface proteins L-, M- and S- are embedded into an ER-derived lipid bilayer. The L- and M-proteins contain the complete S-domain serving as a membrane anchor.

(B) Domain structure of the 3 HBV surface proteins L, M and S.

The L-protein contains the N-terminally myristoylated 107 amino acid preS1-domain, the 55 amino acid preS2-domain and the S-domain containing the 4 transmembrane segments (I-IV).

Figure 2:
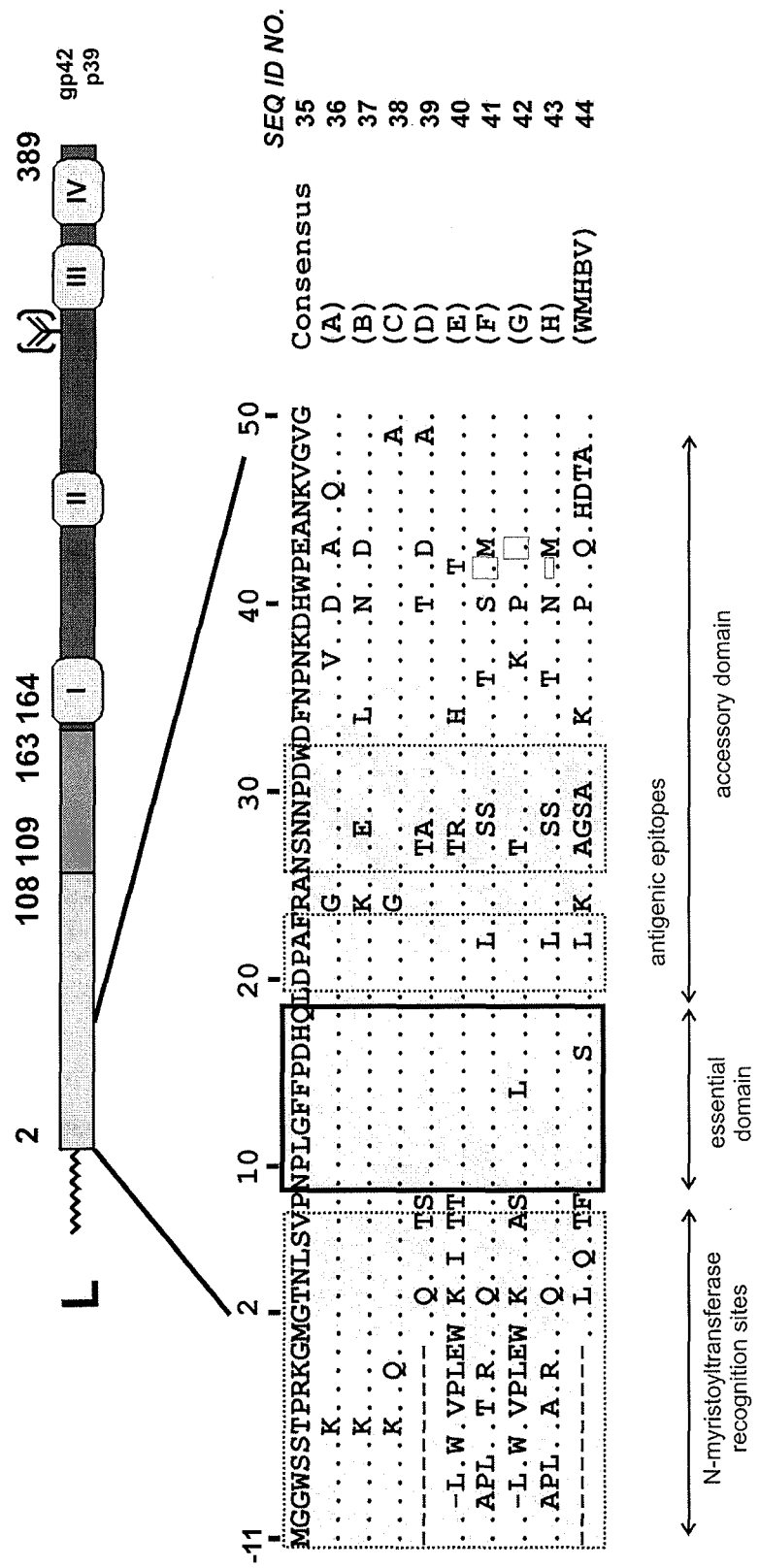

FIG. 2. HBVpreS1 consensus sequence.

At the top: the HBV L-protein with its preS1, preS2 and S-domain is depicted. The N-terminus is myristoylated.

The alignment below shows: the consensus sequence (Consensus; SEQ ID NO:35) and the eight HBV genotypes (A-H; SEQ ID NOS:36-43) as well as the woolly monkey HBV (WMHBV; SEQ ID NO:44) preS sequence encompassing amino acids 2-50. Note that the genotypes A, B, C, E, G and H have eleven additional amino acids at their N-termini, genotype F has 10 additional amino acid residues.

At the bottom, the known functional subdomains are shown.

Please note that HBV genotype C refers to HBV genotype C Q46K.

Figure 3:
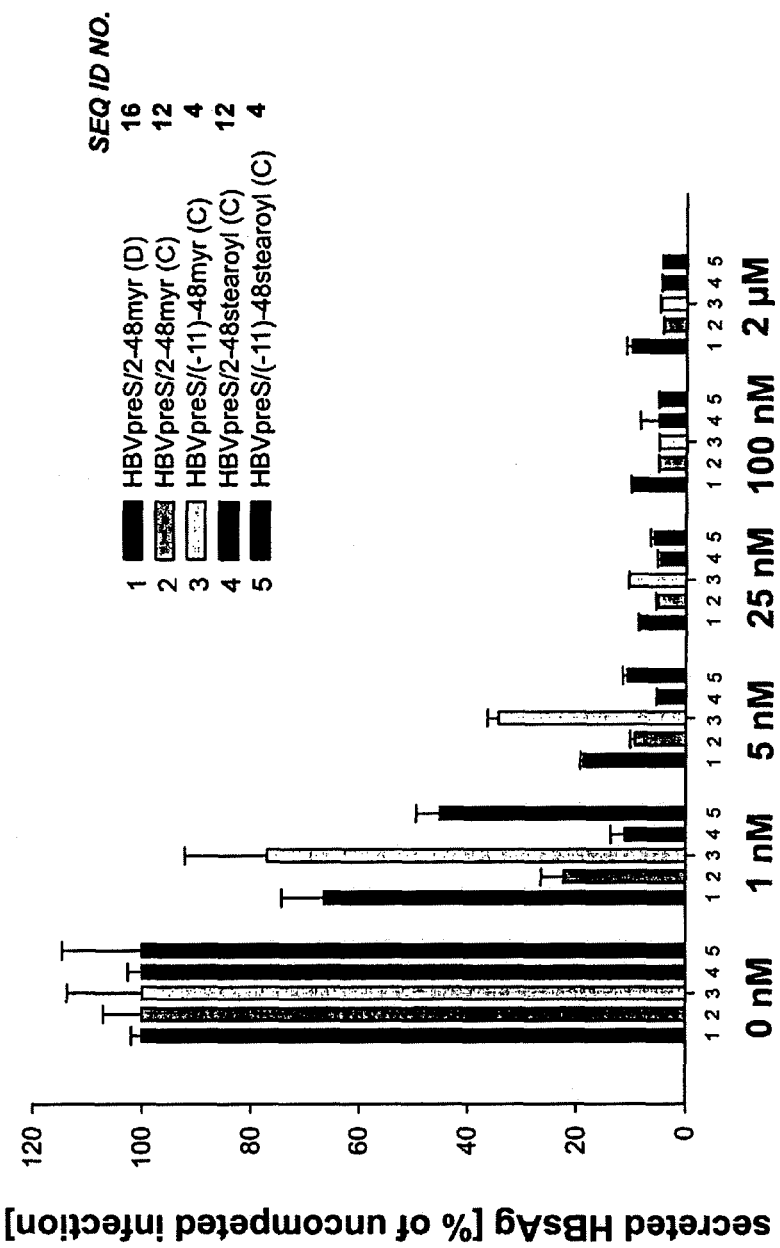

FIG. 3. Comparative infection inhibition assay of myristoylated and stearoylated HBVpreS-derived peptides of the two genotypes C and D.

HepaRG cells were infected either in absence (0 nM) or in the presence of 1, 5, 25, 100 and 2000 nM of HBVpreS/2-48$^{myr}$(D), HBVpreS/2-48$^{myr}$(C), HBVpreS/(−11)-48$^{myr}$(C), HBVpreS/2-48$^{stearoyl}$(C) and HBVpreS/(−11)-48$^{stearoyl}$(C). The infectious inoculum (HBV of genotype D) and the peptides were incubated overnight. After washing, cells were maintained for another 12 days to allow viral gene expression. Cell culture supernatants from day 8-12 were collected and analyzed for secreted HBsAg using a quantitative commercially available ELISA. HBsAg values from the respective uncompleted infection were set to 100% and the degree of infection inhibition is given in % of the uncompleted infection. Wherein (C) or genotype C refers to HBV genotype C Q46K.

Figure 4:
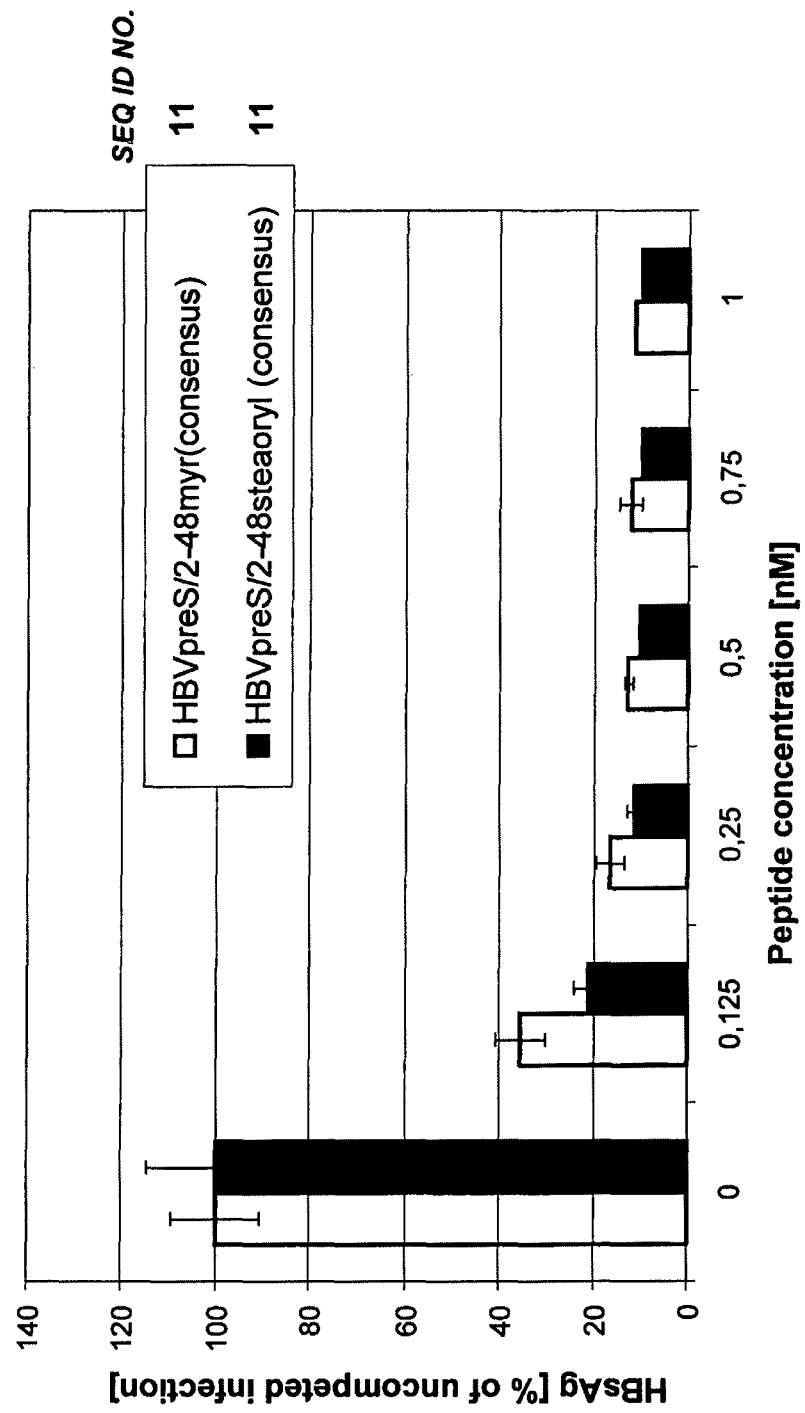

FIG. 4. Infection inhibition assay of myristoylated and stearoylated HBVpreS-derived peptides with the consensus sequence.

HepaRG cells were infected either in absence (0 nM) or in the presence of 0.125; 0.25; 0.5; 0.75 and 1 nM of HBVpreS/2-48$^{myr}$(consensus) and HBVpreS/2-48$^{stearoyl}$(consensus). The infectious inoculum (HBV of genotype D) and the peptides were incubated overnight. After washing, cells were maintained for another 12 days to allow viral gene expression. Cell culture supernatants from day 8-12 were collected and analyzed for secreted HBsAg using a quantitative commercially available ELISA. HBsAg values from the respective uncompleted infection were set to 100% and the degree of infection inhibition is given in % of the uncompleted infection.

Figure 5:
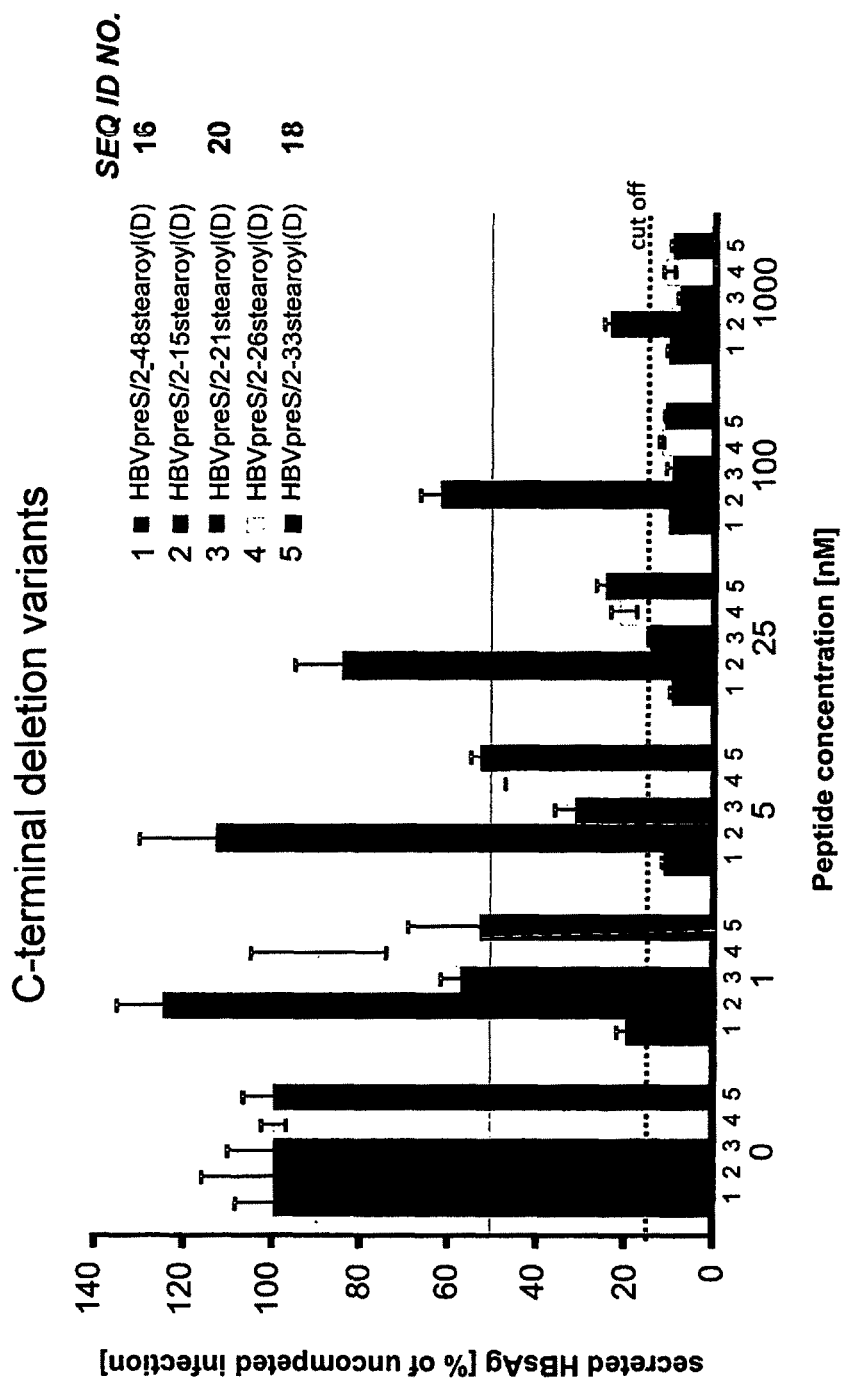

FIG. 5. Comparative infection inhibition assay of C-terminally deleted stearoylated HBVpreS-derived peptides of genotype D.

HepaRG cells were infected either in absence (0 nM) or in the presence of 1, 5, 25, 100 and 1000 nM of HBVpreS/2-48$^{stearoyl}$(D), HBVpreS/2-15$^{stearoyl}$(D), HBVpreS/2-21$^{stearoyl}$(D), HBVpreS/2-26$^{stearoyl}$(D) and HBVpreS/2-33$^{stearoyl}$(D). The infectious inoculum (HBV of genotype D) and the peptides were incubated overnight. After washing, cells were maintained for another 12 days to allow viral gene expression. Cell culture supernatants from day 8-12 were collected and analyzed for secreted HBsAg using a quantitative commercially available ELISA. HBsAg values from the respective uncompleted infection were set to 100% and the degree of infection inhibition is given in % of the uncompleted infection.

Figure 6:
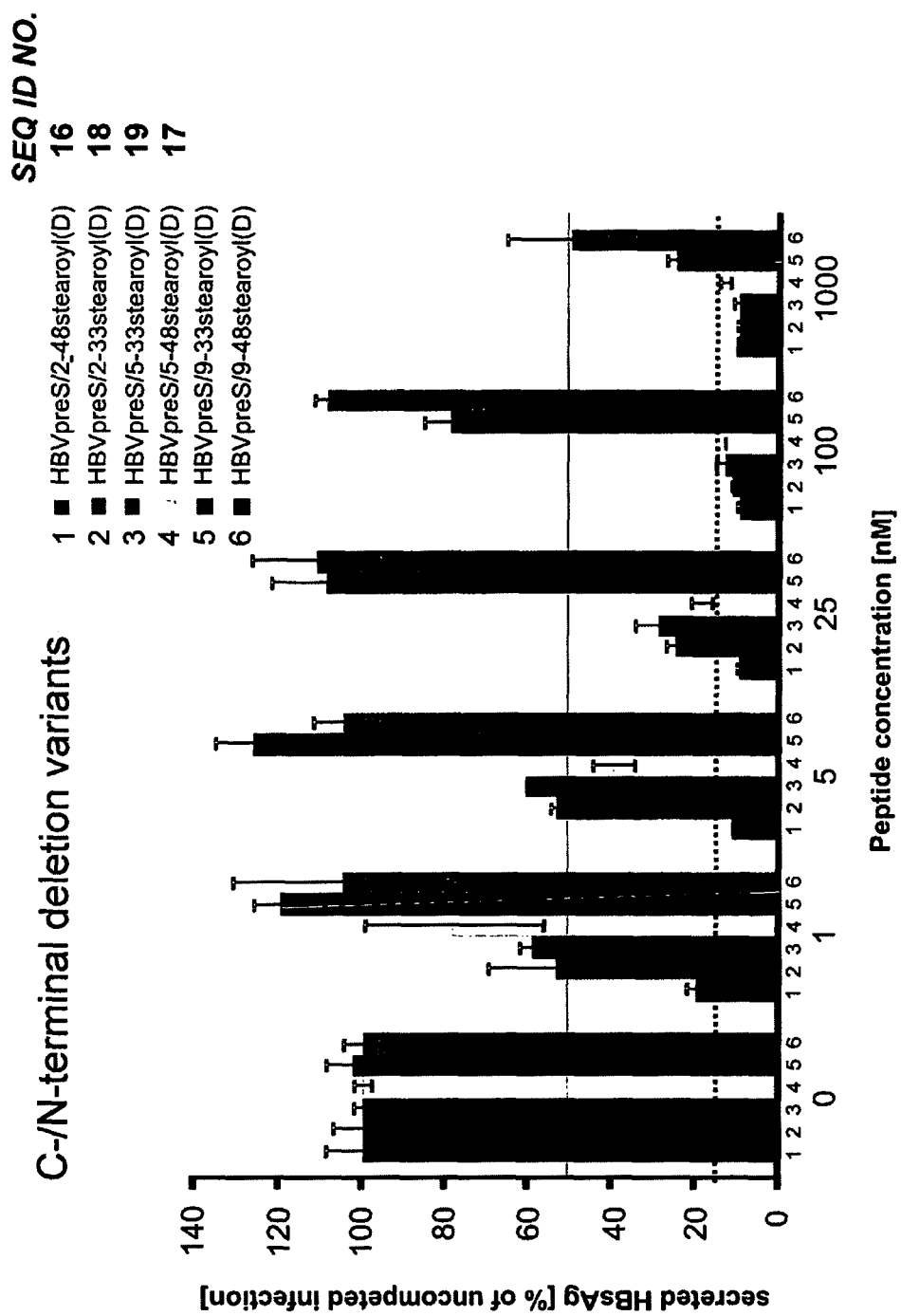

FIG. 6. Comparative infection inhibition assay of N- and C-terminally deleted stearoylated HBVpreS-derived peptides of genotype D.

HepaRG cells were infected either in absence (0 nM) or in the presence of 1, 5, 25, 100 and 1000 nM of HBVpreS/2-48$^{stearoyl}$(D), HBVpreS/2-33$^{stearoyl}$(D), HBVpreS/5-33$^{stearoyl}$(D), HBVpre S/5-48$^{stearoyl}$(D), HBVpreS/9-33$^{stearoyl}$(D) and HBVpreS/9-48$^{stearoyl}$(D). The infectious inoculum (HBV of genotype D) and the peptides were incubated overnight. After washing, cells were maintained for another 12 days to allow viral gene expression. Cell culture supernatants from day 8-12 were collected and analyzed for secreted HBsAg using a quantitative commercially available ELISA. HBsAg values from the respective uncompleted infection were set to 100% and the degree of infection inhibition is given in % of the uncompleted infection.

Figure 7:
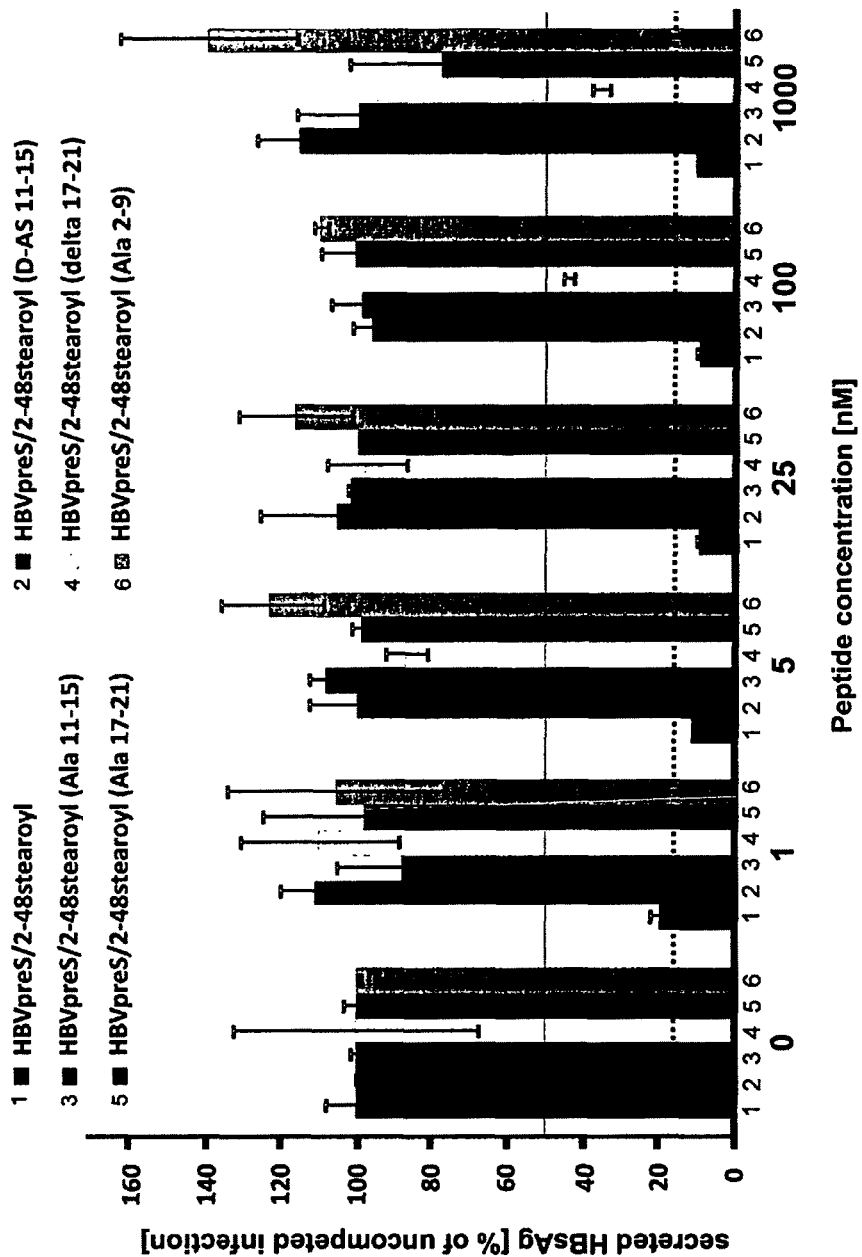

FIG. 7. Comparative infection inhibition assay of internally mutated stearoylated HBVpreS/2-48 peptides of genotype D.

HepaRG cells were infected either in absence (0 nM) or in the presence of 1, 5, 25, 100 and 1000 nM of HBVpreS/2-48$^{stearoyl}$(D), HBVpreS/2-48$^{stearoyl}$(D-AS$^{11-15}$)(D), HBVpreS/2-48$^{stearoyl}$(Ala$^{11-15}$)(D), HBVpreS/2-48$^{stearoyl}$(Δ17-21)(D), HBVpreS/2-48$^{stearoyl}$(Ala$^{17-21}$)(D) and HBVpreS/2-48$^{stearoyl}$(Ala$^{2-9}$)(D). The infectious inoculum (HBV of genotype D) and the peptides were incubated overnight. After washing, cells were maintained for another 12 days to allow viral gene expression. Cell culture supernatants from day 8-12 were collected and analyzed for secreted HBsAg using a quantitative commercially available ELISA. HBsAg values from the respective uncompleted infection were set to 100% and the degree of infection inhibition is given in % of the uncompleted infection.

Figure 8:
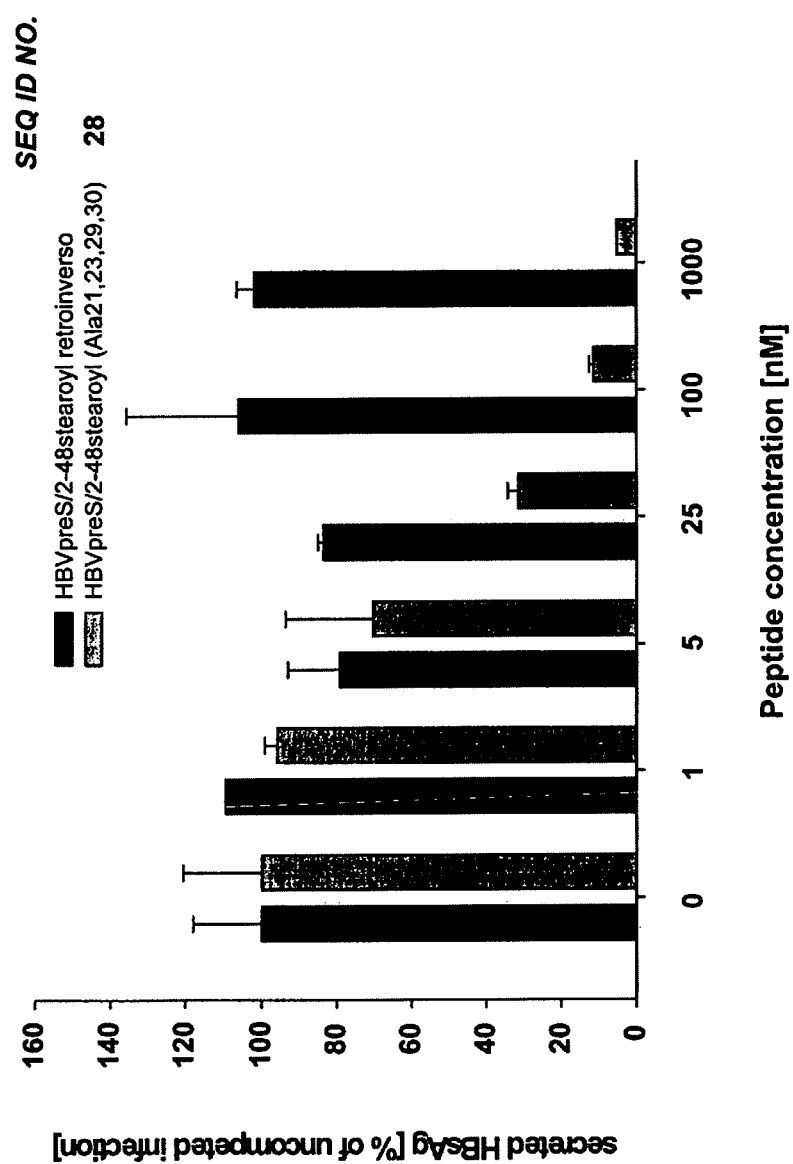

FIG. 8. Comparative infection inhibition assay of internally mutated stearoylated HBVpreS/2-48 peptides of genotype D.

HepaRG cells were infected either in absence (0 nM) or in the presence of 1, 5, 25, 100 and 1000 nM of HBVpreS/2-48$^{stearoyl}$(retroinverso)(D) and HBVpreS/2-48$^{stearoyl}$(Ala$^{21,23,29,30}$)(D). The infectious inoculum (HBV of genotype D) and the peptides were incubated overnight. After washing, cells were maintained for another 12 days to allow viral gene expression. Cell culture supernatants from day 8-12 were collected and analyzed for secreted HBsAg using a quantitative commercially available ELISA. HBsAg values from the respective uncompleted infection were set to 100% and the degree of infection inhibition is given in % of the uncompleted infection.

Figure 9:
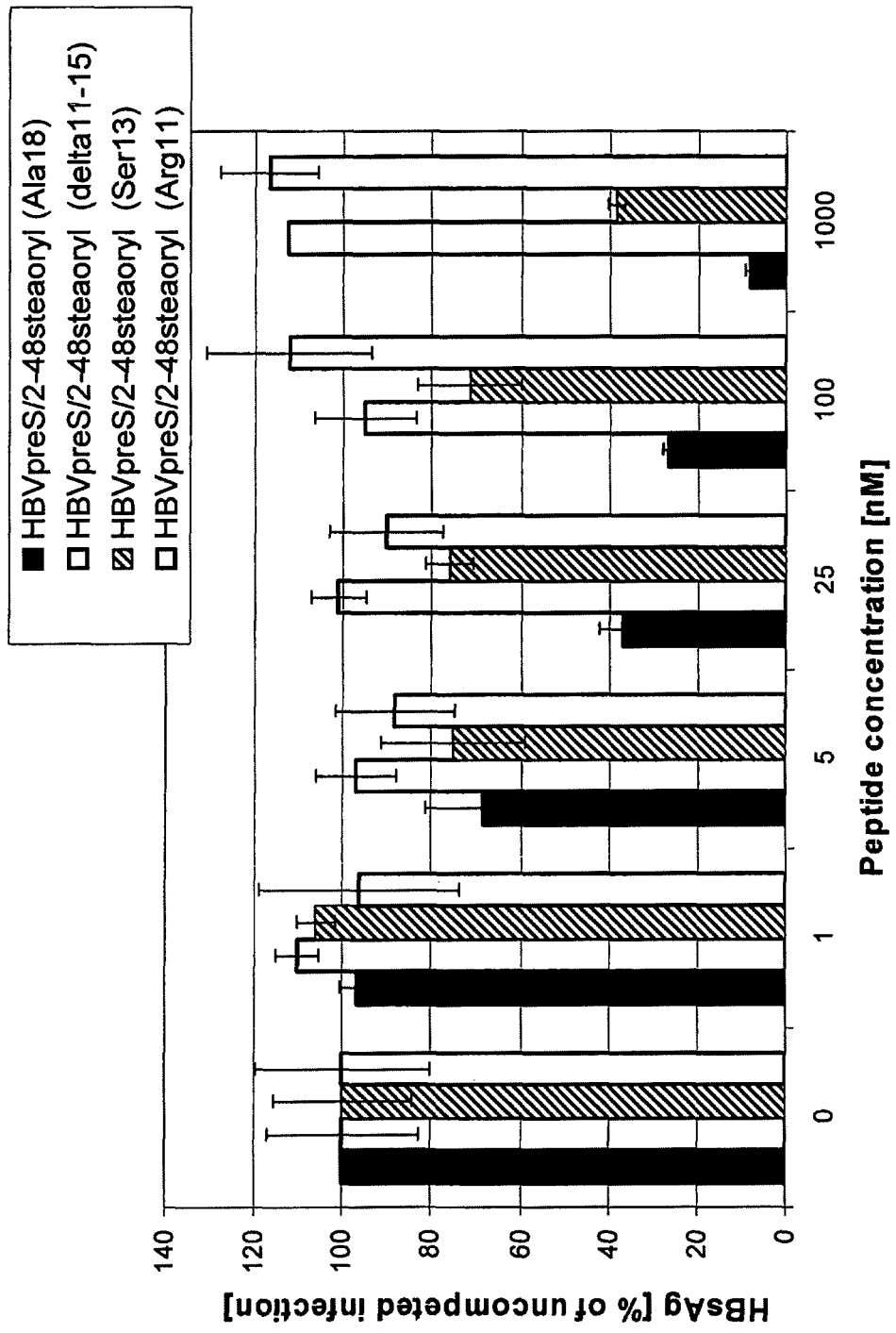

FIG. 9. Further comparative infection inhibition assay of internally mutated stearoylated HBVpreS/2-48 peptides of genotype D.

HepaRG cells were infected either in absence (0 nM) or in the presence of 1, 5, 25, 100 and 1000 nM of HBVpreS/2-48$^{stearoyl}$(Ala$^{18}$)(D), HBVpre S/2-48$^{stearoyl}$(Δ11-15)(D), HBBpreS/2-48$^{stearoyl}$(Ser$^{13}$)(D) and HBVpreS/2-48$^{stearoyl}$(Arg$^{11}$)(D). The infectious inoculum (HBV of genotype D) and the peptides were incubated overnight. After washing, cells were maintained for another 12 days to allow viral gene expression. Cell culture supernatants from day 8-12 were collected and analyzed for secreted HBSAg using a quantitative commercially available ELISA. HBsAg values from the respective uncompleted infection were set to 100% and the degree of infection inhibition is given in % of the uncompleted infection.

Figure 10:
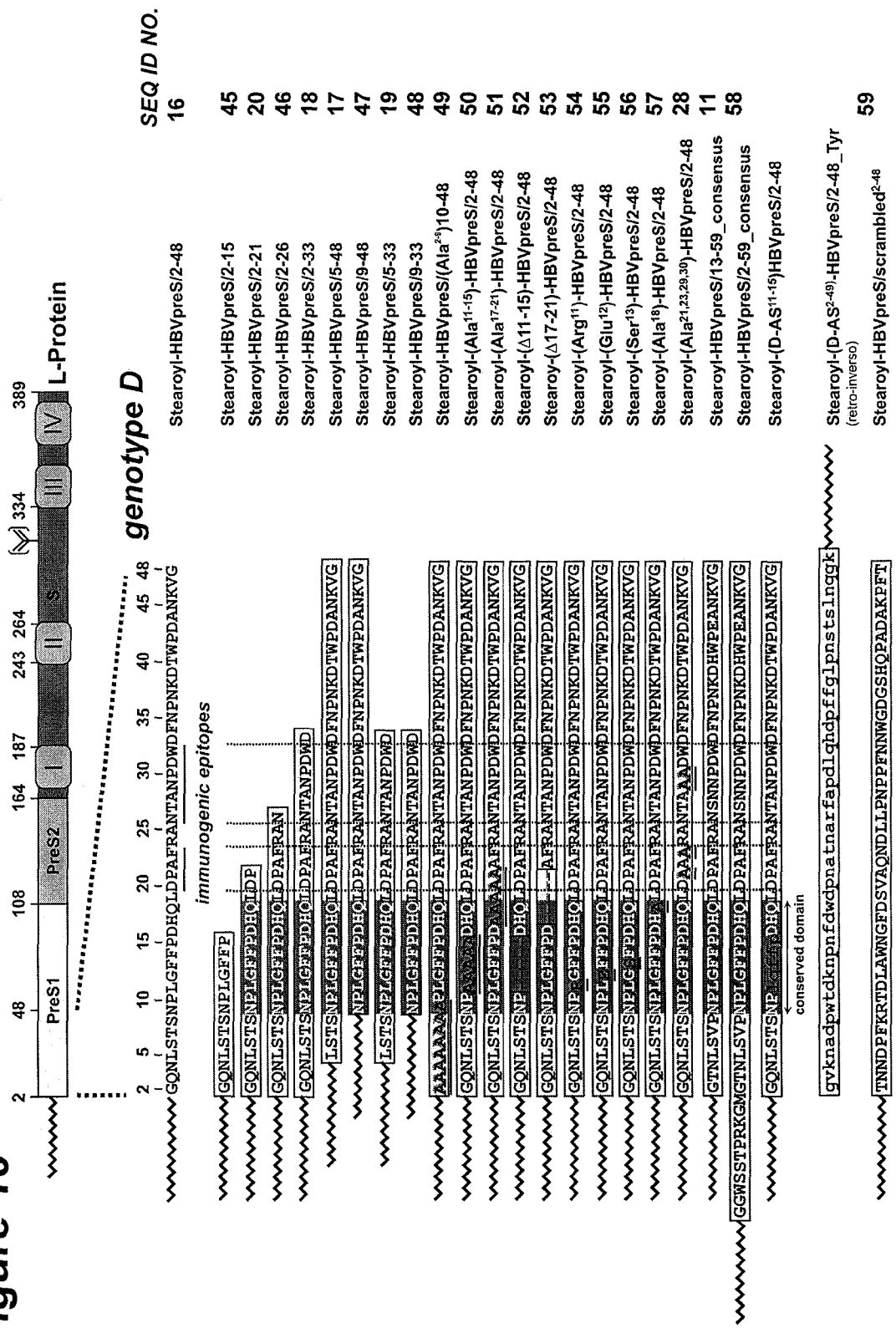

FIG. 10. Stearoylated HBVpreS-derived peptides of genotype D used in this invention (SEQ ID NOS:16, 45, 20, 46, 18, 17, 47, 19, 48-57, 28 and 58-62, respectively).

Figure 11:
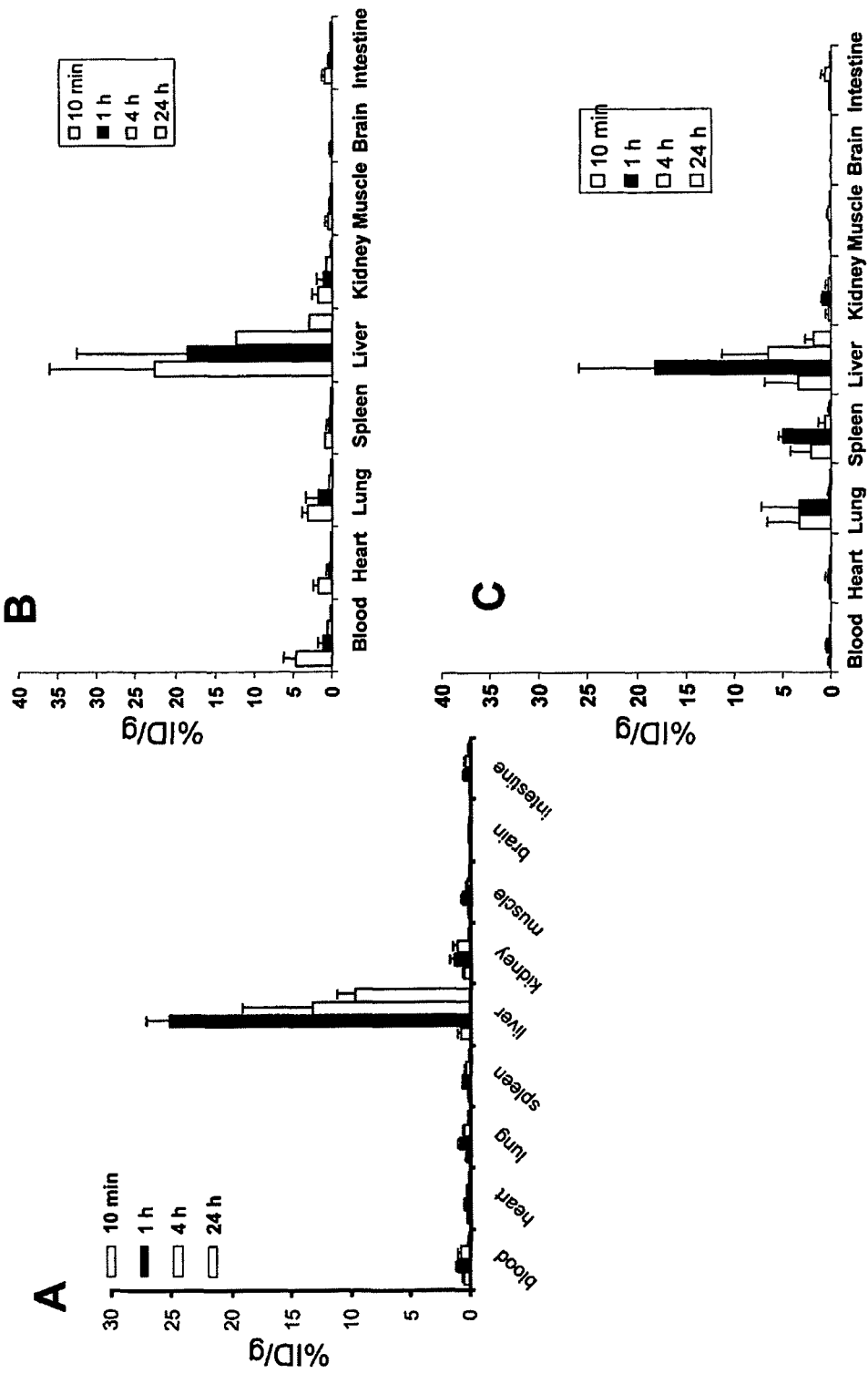

FIG. 11. The hydrophobic modified preS peptides of the invention show an in vivo liver tropism.

A Biodistribution of HBVpreS/2-48 Tyr$^{stearoyl}$(D) in mice.

B Biodistribution of HBVpreS/5-48 D-Tyr$^{stearoyl}$(D) in mice.

C Biodistribution of HBVpreS/2-33-D-Tyr$^{stearoyl}$(D) in mice.

FIG. 12. HBV infection inhibition on HepaRG cells by Myrcludex B, effect of acylation. Myrcludex B refers to HBVpreS/2-48(C), wherein (C) refers to HBV genotype C Q46K. Competitive assay comparing the stearoylated and myristoylated HBVpreS/2-48(C), HBVpreS/2-48$^{myr}$(C) and HBVpreS/2-48$^{stearoyl}$(C). The concentrations tested were below 1 nM in order to have not full competition.

Shown are HBeAg measurements, day 7-14 p.i.

Same reaction and infection conditions as for the experiments shown in FIGS. 3 to 9.

EXAMPLES

Methods

Synthesis of Hydrophobic Modified preS-Derived Peptides of HBV

The synthesis was carried out as described e.g. in (16).

Cell Lines and Primary Cell Cultures.

HepaRG cells were grown in William's E medium supplemented with 10% fetal calf serum (FCS), 100 units/ml penicillin, 100 µg/ml streptomycin, 5 µg/ml insulin and 5×10$^{-5}$ M hydrocortisone hemisuccinate (16). Cells were passaged 1/5 every two weeks by trypsination. Two to three weeks before infection cell differentiation was induced by adding 2% DMSO into the maintenance medium. The medium was exchanged every 2-3 days.

Infection Competition Assays.

As an infectious inoculum, a 50-fold concentrated culture supernatant of HepG2 clone 2.2.15 (23) cells was used, because of an unlimited supply and a constant quality. It was prepared from freshly collected supernatants by precipitating viral particles in the presence of 6% polyethylene glycol (PEG) 8000. The pellet was resuspended in phosphate buffered saline (PBS) containing 25% FCS. Aliquots were stored at −80° C. Differentiated HepaRG cells or PHH were incubated with the concentrated infectious source, 10-fold diluted in culture medium supplemented with 4% PEG 8000 (Sigma), for 20 h at 37° C. At the end of the incubation, cells were washed three times with the culture medium and maintained in the presence of 2% DMSO and 5×10$^{-5}$ M hydrocortisone hemisuccinate and harvested at indicated times.

Competition experiments were performed in 12-well plates. Approximately 1×10$^6$ cells were first pre-incubated for 30 min with chemically synthesized HBV derived peptides followed by a co-incubation of cells with peptide and virus for 20 h. All competition series were performed at least twice and the results of one representative experiment are shown in each case (see FIGS. 3 to 7).

HepaRG cells were infected either in absence (0 nM) or in the presence of
1, 5, 25, 100 and 2000 nM of
  HBVpreS/2-48$^{myr}$(D),
  HBVpreS/2-48$^{myr}$(C),
  HBVpreS/(−11)-48$^{myr}$(C),
  HBVpreS/2-48$^{stearoyl}$(C) and
  HBVpreS/(−11)-48$^{stearoyl}$(C); or
0.125; 0.25; 0.5; 0.75 and 1 nM of
  HBVpreS/2-48$^{myr}$(consensus),
  HBVpreS/2-48$^{stearoyl}$(consensus),
1, 5, 25, 100 and 1000 nM of
  HBVpreS/2-48$^{stearoyl}$(D),
  HBVpreS/2-15$^{stearoyl}$(D),
  HBVpreS/2-21$^{stearoyl}$(D),
  HBVpreS/2-26$^{stearoyl}$(D) and
  HBVpreS/2-33$^{stearoyl}$(D); or
1, 5, 25, 100 and 1000 nM of
  HBVpreS/2-48$^{stearoyl}$(D),
  HBVpreS/2-33$^{stearoyl}$(D),
  HBVpreS/5-33$^{stearoyl}$(D),
  HBVpreS/5-48$^{stearoyl}$(D),
  HBVpreS/9-33$^{stearoyl}$(D) and
  HBVpreS/9-48$^{stearoyl}$(D); or
1, 5, 25, 100 and 1000 nM of
  HBVpreS/2-48$^{stearoyl}$(D),
  HBVpreS/2-48$^{stearoyl}$(D-AS$^{11-15}$)(D),
  HBVpreS/2-48$^{stearoyl}$(Ala$^{11-15}$)(D),
  HBVpreS/2-48$^{stearoyl}$(Δ17-21)(D),
  HBVpreS/2-48$^{stearoyl}$(Ala$^{17-21}$)(D); or
1, 5, 25, 100 and 1000 nM of
  HBVpreS/2-48$^{stearoyl}$(retroinverso)(D) and
  HBVpreS/2-48$^{stearoyl}$(Ala$^{21,23,29,30}$)(D); or
1, 5, 25, 100 and 1000 nM of
  HBVpreS/2-48$^{stearoyl}$(Ala$^{18}$)(D),
  HBVpreS/2-48$^{stearoyl}$(Δ11-15)(D),
  HBVpreS/2-48$^{stearoyl}$(Ser$^{13}$)(D),
  HBVpreS/2-48$^{stearoyl}$(Arg$^{11}$)(D).; or
50, 100, 150, 250 and 1000 pM (0.05, 0.1, 0.25 and 1 nM) of
  HBVpreS/2-48$^{myr}$(C) and
  HBVpreS/2-48$^{stearoyl}$(C),
wherein (C) refers to HBV genotype C Q46K.

The infectious inoculum (HBV of genotype D) and the peptides were incubated overnight. After washing, cells were maintained for another 12 days to allow viral gene expression. Cell culture supernatants from day 8-12 were collected and analyzed for secreted HBSAg using a quantitative commercially available ELISA. HBsAg values from the respective uncompleted infection were set to 100% and the degree of infection inhibition is given in % of the uncompleted infection.

Results are shown in FIGS. 3 to 9 and 12 as wells Tables 3 to 9.

Biodistribution of the Hydrophobic Modified preS-Derived Peptides

The biodistribution of the hydrophobic modified preS-derived peptides was studied in male NMRI mice. All experiments were performed in compliance with German laws. The peptides, containing an additional Tyr-residue at the C-terminal end were labelled with $^{131}$I (Amersham Biosciences, Freiburg, Germany) by the chloramine-T method and purified by HPLC. The labelled peptides were subcutaneously administered by injection of a solution in 50% DMSO. At selected times mice were sacrificed and the radioactivity contained in the blood, heart, lung, spleen, liver, kidney, muscle and brain was measured in a γ-counter (Canberra Packard, Rüsselsheim, Germany) and expressed as a percentage of injected dose per gram of tissue (% ID/g).

Stability Assessment of the Hydrophobic Modified preS-Derived Peptides After Extraction from the Liver To determine the peptide stability in the liver $^{131}$I labelled HBVpreS/2-48$^{myr}$ (D) was extracted from one liver lobe 24 h post subcutaneous injection. To that aim, 1 ml water per gram frozen liver tissue was added to the sample. After homogenization an equal volume of acetonitrile was added and the homogenization was repeated. After centrifugation (2×10 min at 4000×g) this solution was separated on a reverse phase HPLC column and the radioactivity of each fraction was quantified in a gamma counter.

The features disclosed in the foregoing description, in the claims and/or in the accompanying drawings may, both separately and in any combination thereof, be material for realizing the invention in diverse forms thereof.

REFERENCES

1. Shepard, C. W., Simard, E. P., Finelli, L., Fiore, A. E. & Bell, B. P. Hepatitis B virus infection: epidemiology and vaccination. *Epidemiol Rev* 28, 112-125 (2006).
2. Root, M. J. & Steger, H. K. HIV-1 gp41 as a target for viral entry inhibition. *Curr Pharm Des* 10, 1805-1825 (2004).
3. Chan, H. L. & Sung, J. J. Hepatocellular carcinoma and hepatitis B virus. *Semin Liver Dis* 26, 153-161 (2006).
4. Zoulim, F. Antiviral therapy of chronic hepatitis B. *Antiviral Res* 71, 206-215 (2006).
5. Seeger, C. & Mason, W. S. Hepatitis B virus biology. *Microbiol Mol Biol Rev* 64, 51-68 (2000).
6. Nassal, M. Hepatitis B virus morphogenesis. *Curr Top Microbiol Immunol* 214, 297-337 (1996).
7. Gripon, P., Le Seyec, J., Rumin, S. & Guguen-Guillouzo, C. Myristylation of the hepatitis B virus large surface protein is essential for viral infectivity. *Virology* 213, 292-299 (1995).
8. Le Seyec, J., Chouteau, P., Cannie, I., Guguen-Guillouzo, C. & Gripon, P. Infection process of the hepatitis B virus depends on the presence of a defined sequence in the pre-S1 domain. *J Virol* 73, 2052-2057 (1999).
9. Glebe, D. & Urban, S. Viral and cellular determinants involved in hepadnaviral entry. *World J Gastroenterol* 13, 22-38 (2007).
10. Gripon, P. et al. Infection of a human hepatoma cell line by hepatitis B virus. *Proc Natl Acad Sci USA* 99, 15655-15660 (2002).
11. B. W. Erickson and R. B. Merrifield, 1976.
12. Gausepohl, H. et al. *Int. J. Prot. Pept. Res.* 34, 287-294 (1989).
13. Freireich, E. J., Gehan, E. A., Rall, D. P., Schmidt, L. H. & Skipper, H. E. Quantitative comparison of toxicity of anticancer agents in mouse, rat, hamster, dog, monkey, and man. *Cancer Chemother Rep* 50, 219-244 (1966).
14. Locarnini, S. et al. Management of antiviral resistance in patients with chronic hepatitis B. *Antivir Ther* 9, 679-693 (2004).
15. Engelke, M. et al. Characterization of a hepatitis B and hepatitis delta virus receptor binding site. *Hepatology* 43, 750-760 (2006).
16. Gripon, P., Cannie, I. & Urban, S. Efficient inhibition of hepatitis B virus infection by acylated peptides derived from the large viral surface protein. *J Virol* 79, 1613-1622 (2005).
17. Barrera, A., Guerra, B., Notvall, L. & Lanford, R. E. Mapping of the hepatitis B virus pre-S1 domain involved in receptor recognition. *J Virol* 79, 9786-9798 (2005).
18. Dandri, M. & Petersen, J. Hepatitis B virus cccDNA clearance: killing for curing? *Hepatology* 42, 1453-1455 (2005).
19. Dandri, M. et al. Chronic infection with hepatitis B viruses and antiviral drug evaluation in uPA mice after liver repopulation with tupaia hepatocytes. *J Hepatol* 42, 54-60 (2005).
20. Taylor, J. M. Hepatitis delta virus. *Virology* 344, 71-76 (2006).
21. Glebe, D. Attachment sites and neutralising epitopes of hepatitis B virus. *Minerva Gastroenterol Dietol* 52, 3-21 (2006).
22. Gripon P, Rumin S, Urban S, Le S J, Glaise D, Cannie I, Guyomard C, Lucas J, Trepo C, Guguen-Guillouzo C. Infection of a human hepatoma cell line by hepatitis B virus. *Proc Natl Acad Sci USA* 99, 15655-15660 (2002).
23. Glebe D, Urban S, Knoop E V, Cag N, Krass P, Grun S, Bulavaite A, Sasnauskas K, Gerlich W H. Mapping of the hepatitis B virus attachment site by use of infection-inhibiting preS1 lipopeptides and tupaia hepatocytes. *Gastroenterology* 129, 234-245 (2005).

The invention claimed is:

1. A hydrophobic modified preS-derived peptide of hepatitis B virus (HBV) of the formula $$H_m\text{—}P\text{—}R_n,$$

wherein
- P is said preS-derived peptide consisting of the amino acid sequence of SEQ ID NO:11 or SEQ ID NO:12;
- H is a hydrophobic modification of said preS-derived peptide P, which is N-terminal of P and selected from acylation and addition of hydrophobic moieties;
- R is a C-terminal modification of said preS-derived peptide P that protects the peptide from degradation;
- m is at least 1; and
- n is 0 or at least 1.

2. The hydrophobic modified preS-derived peptide according to claim 1, wherein P consists of the amino acid sequence of SEQ ID NO:11.

3. The hydrophobic modified preS-derived peptide according to claim 1, wherein P consists of the amino acid sequence of SEQ ID NO:12.

4. The hydrophobic modified preS-derived peptide according to claim 2, wherein H, R, or both H and R are linked to P via a linker or spacer.

5. The hydrophobic modified preS-derived peptide according to claim 2, wherein H is a hydrophobic modification by acylation.

6. The hydrophobic modified preS-derived peptide according to claim 5, wherein H is a hydrophobic modification by acylation with myristoyl (C14), palmitoyl (C16) or stearoyl (C18).

7. The hydrophobic modified preS-derived peptide according to claim 5, wherein the acylation is selected from acylation with carboxylic acids, fatty acids, C8 to C22 fatty acids, and amino acids with lipophilic side chains.

8. The hydrophobic modified preS-derived peptide according to claim 2, wherein H is a hydrophobic modification by addition of hydrophobic moieties selected from cholesterol, derivatives of cholesterol, phospholipids, glycolipids, glycerol esters, steroids, ceramides, isoprene derivatives, adamantane, farnesol, aliphatic groups, and polyaromatic compounds.

9. The hydrophobic modified preS-derived peptide according to claim 2, wherein R is a modification with a moiety selected from amide, D-amino acid, modified amino acid, cyclic amino acid, natural polymer, synthetic polymer, and glycan.

10. The hydrophobic modified preS-derived peptide according to claim 9, wherein the moiety is polyethylene glycol (PEG).

11. The hydrophobic modified preS-derived peptide according to claim 2, which carries a label.

12. The hydrophobic modified preS-derived peptide according to claim 11, wherein the label is selected from a fluorescent dye, a radioisotope and a contrast agent.

13. The hydrophobic modified preS-derived peptide of claim 2, which is fused to a peptide or protein.

14. The hydrophobic modified preS-derived peptide of claim 13, wherein the peptide or protein is selected from albumin and Fc domains of human IgGs.

15. The hydrophobic modified preS-derived peptide of claim 2, which inhibits HBV and/or HDV cell entry.

16. A method of diagnosing, treating, inhibiting or preventing HBV and/or HDV infection, primary HBV and/or HDV infection, hepatitis B and/or D, or chronic hepatitis B and/or D, said method comprising administering to a subject in need thereof a hydrophobic modified preS-derived peptide according to claim 1.

17. The method of claim 16, wherein HBV infection by any HBV genotype is inhibited or prevented.

18. The method of claim 17, wherein the peptide is administered in a therapeutically effective amount in the range of 10 µg to 1 mg per kg body weight.

19. The method of claim 18, wherein the therapeutically effective amount is in the range of 10 µg to 100 µg.

20. The method of claim 17, wherein the route of administration is selected from subcutaneous, intravenous, oral, nasal, intramuscular, transdermal, inhalative, and by suppository.

21. A pharmaceutical composition comprising at least one hydrophobic modified preS-derived peptide of HBV according to claim 2; and a pharmaceutically acceptable carrier, an excipient, or combinations thereof.

22. A vaccine composition comprising at least one hydrophobic modified preS-derived peptide of HBV according to claim 2, and a pharmaceutically acceptable carrier, an excipient, or combinations thereof.

23. The hydrophobic modified preS-derived peptide according to claim 3, wherein H, R, or both H and R are linked to P via a linker or spacer.

24. The hydrophobic modified preS-derived peptide according to claim 3, wherein H is a hydrophobic modification by acylation.

25. The hydrophobic modified preS-derived peptide according to claim 24, wherein H is a hydrophobic modification by acylation with myristoyl (C14), palmitoyl (C16) or stearoyl (C18).

26. The hydrophobic modified preS-derived peptide according to claim 24, wherein the acylation is selected from acylation with carboxylic acids, fatty acids, C8 to C22 fatty acids, and amino acids with lipophilic side chains.

27. The hydrophobic modified preS-derived peptide according to claim 3, wherein H is a hydrophobic modification by addition of hydrophobic moieties selected from cholesterol, derivatives of cholesterol, phospholipids, glycolipids, glycerol esters, steroids, ceramides, isoprene derivatives, adamantane, farnesol, aliphatic groups, and polyaromatic compounds.

28. The hydrophobic modified preS-derived peptide according to claim 3, wherein R is a modification with a moiety selected from amide, D-amino acid, modified amino acid, cyclic amino acid, natural polymer, synthetic polymer, and glycan.

29. The hydrophobic modified preS-derived peptide according to claim 28, wherein the moiety is polyethylene glycol (PEG).

30. The hydrophobic modified preS-derived peptide according to claim 3, which carries a label.

31. The hydrophobic modified preS-derived peptide according to claim 30, wherein the label is selected from a fluorescent dye, a radioisotope and a contrast agent.

32. The hydrophobic modified preS-derived peptide of claim 3, which is fused to a peptide or protein.

33. The hydrophobic modified preS-derived peptide of claim 32, wherein the peptide or protein is selected from albumin and Fc domains of human IgGs.

34. The hydrophobic modified preS-derived peptide of claim 3, which inhibits HBV and/or HDV cell entry.

35. A method of diagnosing, treating, inhibiting or preventing HBV and/or HDV infection, primary HBV and/or HDV infection, hepatitis B and/or D, or chronic hepatitis B and/or D, said method comprising administering to a subject in need thereof a hydrophobic modified preS-derived peptide according to claim 3.

36. The method of claim 35, wherein HBV infection by any HBV genotype is inhibited or prevented.

37. The method of claim 36, wherein the peptide is administered in a therapeutically effective amount in the range of 10 µg to 1 mg per kg body weight.

38. The method of claim 37, wherein the therapeutically effective amount is in the range of 10 µg to 100 µg.

39. The method of claim 36, wherein the route of administration is selected from subcutaneous, intravenous, oral, nasal, intramuscular, transdermal, inhalative, and by suppository.

40. A pharmaceutical composition comprising at least one hydrophobic modified preS-derived peptide of HBV according to claim 3; and a pharmaceutically acceptable carrier, an excipient, or combinations thereof.

41. A vaccine composition comprising at least one hydrophobic modified preS-derived peptide of HBV according to claim 3, and a pharmaceutically acceptable carrier, an excipient, or combinations thereof.

* * * * *

SEQUENCE LISTING

```
<160> NUMBER OF SEQ ID NOS: 59

<210> SEQ ID NO 1
<211> LENGTH: 59
<212> TYPE: PRT
<213> ORGANISM: Artificial Sequence
<220> FEATURE:
<223> OTHER INFORMATION: synthetic hepatitis B virus (HBV) preS
      consensus sequence (positions (-11) to 48)

<400> SEQUENCE: 1

Met Gly Gly Trp Ser Ser Thr Pro Arg Lys Gly Met Gly Thr Asn Leu
```

```
                1               5                   10                  15
Ser Val Pro Asn Pro Leu Gly Phe Phe Pro Asp His Gln Leu Asp Pro
                20                  25                  30

Ala Phe Arg Ala Asn Ser Asn Asn Pro Asp Trp Asp Phe Asn Pro Asn
            35                  40                  45

Lys Asp His Trp Pro Glu Ala Asn Lys Val Gly
        50                  55

<210> SEQ ID NO 2
<211> LENGTH: 59
<212> TYPE: PRT
<213> ORGANISM: Hepatitis B virus
<220> FEATURE:
<223> OTHER INFORMATION: hepatitis B virus (HBV) preS genotype A

<400> SEQUENCE: 2

Met Gly Gly Trp Ser Ser Lys Pro Arg Lys Gly Met Gly Thr Asn Leu
1               5                   10                  15

Ser Val Pro Asn Pro Leu Gly Phe Phe Pro Asp His Gln Leu Asp Pro
                20                  25                  30

Ala Phe Gly Ala Asn Ser Asn Asn Pro Asp Trp Asp Phe Asn Pro Val
            35                  40                  45

Lys Asp Asp Trp Pro Ala Ala Asn Gln Val Gly
        50                  55

<210> SEQ ID NO 3
<211> LENGTH: 59
<212> TYPE: PRT
<213> ORGANISM: Hepatitis B virus
<220> FEATURE:
<223> OTHER INFORMATION: hepatitis B virus (HBV) preS genotype B

<400> SEQUENCE: 3

Met Gly Gly Trp Ser Ser Lys Pro Arg Lys Gly Met Gly Thr Asn Leu
1               5                   10                  15

Ser Val Pro Asn Pro Leu Gly Phe Phe Pro Asp His Gln Leu Asp Pro
                20                  25                  30

Ala Phe Lys Ala Asn Ser Glu Asn Pro Asp Trp Asp Leu Asn Pro His
            35                  40                  45

Lys Asp Asn Trp Pro Asp Ala Asn Lys Val Gly
        50                  55

<210> SEQ ID NO 4
<211> LENGTH: 59
<212> TYPE: PRT
<213> ORGANISM: Artificial Sequence
<220> FEATURE:
<223> OTHER INFORMATION: synthetic hepatitis B virus (HBV) preS sequence
      positions (-11) to 48 corresponding to genotype C
      except position 46 Gln to Lys (Q46K)

<400> SEQUENCE: 4

Met Gly Gly Trp Ser Ser Lys Pro Arg Gln Gly Met Gly Thr Asn Leu
1               5                   10                  15

Ser Val Pro Asn Pro Leu Gly Phe Phe Pro Asp His Gln Leu Asp Pro
                20                  25                  30

Ala Phe Gly Ala Asn Ser Asn Asn Pro Asp Trp Asp Phe Asn Pro Asn
            35                  40                  45

Lys Asp His Trp Pro Glu Ala Asn Lys Val Gly
        50                  55
```

<210> SEQ ID NO 5
<211> LENGTH: 48
<212> TYPE: PRT
<213> ORGANISM: Hepatitis B virus
<220> FEATURE:
<223> OTHER INFORMATION: hepatitis B virus (HBV) preS genotype D

<400> SEQUENCE: 5

Met Gly Gln Asn Leu Ser Thr Ser Asn Pro Leu Gly Phe Phe Pro Asp
1               5                   10                  15

His Gln Leu Asp Pro Ala Phe Arg Ala Asn Thr Ala Asn Pro Asp Trp
            20                  25                  30

Asp Phe Asn Pro Asn Lys Asp Thr Trp Pro Asp Ala Asn Lys Val Gly
        35                  40                  45

<210> SEQ ID NO 6
<211> LENGTH: 58
<212> TYPE: PRT
<213> ORGANISM: Hepatitis B virus
<220> FEATURE:
<223> OTHER INFORMATION: hepatitis B virus (HBV) preS genotype E

<400> SEQUENCE: 6

Met Gly Leu Ser Trp Thr Val Pro Leu Glu Trp Gly Lys Asn Ile Ser
1               5                   10                  15

Thr Thr Asn Pro Leu Gly Phe Phe Pro Asp His Gln Leu Asp Pro Ala
            20                  25                  30

Phe Arg Ala Asn Thr Arg Asn Pro Asp Trp Asp His Asn Pro Asn Lys
        35                  40                  45

Asp His Trp Thr Glu Ala Asn Lys Val Gly
    50                  55

<210> SEQ ID NO 7
<211> LENGTH: 59
<212> TYPE: PRT
<213> ORGANISM: Hepatitis B virus
<220> FEATURE:
<223> OTHER INFORMATION: hepatitis B virus (HBV) preS genotype F

<400> SEQUENCE: 7

Met Gly Ala Pro Leu Ser Thr Thr Arg Arg Gly Met Gly Gln Asn Leu
1               5                   10                  15

Ser Val Pro Asn Pro Leu Gly Phe Phe Pro Asp His Gln Leu Asp Pro
            20                  25                  30

Leu Phe Arg Ala Asn Ser Ser Ser Pro Asp Trp Asp Phe Asn Thr Asn
        35                  40                  45

Lys Asp Ser Trp Pro Met Ala Asn Lys Val Gly
    50                  55

<210> SEQ ID NO 8
<211> LENGTH: 58
<212> TYPE: PRT
<213> ORGANISM: Hepatitis B virus
<220> FEATURE:
<223> OTHER INFORMATION: hepatitis B virus (HBV) preS genotype G

<400> SEQUENCE: 8

Met Gly Leu Ser Trp Thr Val Pro Leu Glu Trp Gly Lys Asn Leu Ser
1               5                   10                  15

Ala Ser Asn Pro Leu Gly Phe Leu Pro Asp His Gln Leu Asp Pro Ala
            20                  25                  30

```
Phe Arg Ala Asn Thr Asn Asn Pro Asp Trp Asp Phe Asn Pro Lys Lys
        35                  40                  45

Asp Pro Trp Pro Glu Ala Asn Lys Val Gly
     50                  55

<210> SEQ ID NO 9
<211> LENGTH: 59
<212> TYPE: PRT
<213> ORGANISM: Hepatitis B virus
<220> FEATURE:
<223> OTHER INFORMATION: hepatitis B virus (HBV) preS genotype H

<400> SEQUENCE: 9

Met Gly Ala Pro Leu Ser Thr Ala Arg Arg Gly Met Gly Gln Asn Leu
1               5                   10                  15

Ser Val Pro Asn Pro Leu Gly Phe Phe Pro Asp His Gln Leu Asp Pro
            20                  25                  30

Leu Phe Arg Ala Asn Ser Ser Ser Pro Asp Trp Asp Phe Asn Thr Asn
        35                  40                  45

Lys Asp Asn Trp Pro Met Ala Asn Lys Val Gly
     50                  55

<210> SEQ ID NO 10
<211> LENGTH: 48
<212> TYPE: PRT
<213> ORGANISM: Woolly Monkey Hepatitis B virus
<220> FEATURE:
<223> OTHER INFORMATION: woolly monkey hepatitis B virus (WMHBV) preS
      sequence

<400> SEQUENCE: 10

Met Gly Leu Asn Gln Ser Thr Phe Asn Pro Leu Gly Phe Phe Pro Ser
1               5                   10                  15

His Gln Leu Asp Pro Leu Phe Lys Ala Asn Ala Gly Ser Ala Asp Trp
            20                  25                  30

Asp Lys Asn Pro Asn Lys Asp Pro Trp Pro Gln Ala His Asp Thr Ala
        35                  40                  45

<210> SEQ ID NO 11
<211> LENGTH: 47
<212> TYPE: PRT
<213> ORGANISM: Artificial Sequence
<220> FEATURE:
<223> OTHER INFORMATION: synthetic hepatitis B virus (HBV) preS
      consensus sequence residues 2 to 48

<400> SEQUENCE: 11

Gly Thr Asn Leu Ser Val Pro Asn Pro Leu Gly Phe Phe Pro Asp His
1               5                   10                  15

Gln Leu Asp Pro Ala Phe Arg Ala Asn Ser Asn Pro Asp Trp Asp
            20                  25                  30

Phe Asn Pro Asn Lys Asp His Trp Pro Glu Ala Asn Lys Val Gly
        35                  40                  45

<210> SEQ ID NO 12
<211> LENGTH: 47
<212> TYPE: PRT
<213> ORGANISM: Artificial Sequence
<220> FEATURE:
<223> OTHER INFORMATION: synthetic hepatitis B virus (HBV) preS genotype
      C residues 2 to 48

<400> SEQUENCE: 12
```

Gly Thr Asn Leu Ser Val Pro Asn Pro Leu Gly Phe Phe Pro Asp His
1               5                   10                  15

Gln Leu Asp Pro Ala Phe Gly Ala Asn Ser Asn Asn Pro Asp Trp Asp
            20                  25                  30

Phe Asn Pro Asn Lys Asp His Trp Pro Glu Ala Asn Lys Val Gly
        35                  40                  45

<210> SEQ ID NO 13
<211> LENGTH: 20
<212> TYPE: PRT
<213> ORGANISM: Artificial Sequence
<220> FEATURE:
<223> OTHER INFORMATION: synthetic hepatitis B virus (HBV) preS genotype
      C residues 2 to 21

<400> SEQUENCE: 13

Gly Thr Asn Leu Ser Val Pro Asn Pro Leu Gly Phe Phe Pro Asp His
1               5                   10                  15

Gln Leu Asp Pro
            20

<210> SEQ ID NO 14
<211> LENGTH: 17
<212> TYPE: PRT
<213> ORGANISM: Artificial Sequence
<220> FEATURE:
<223> OTHER INFORMATION: synthetic hepatitis B virus (HBV) preS genotype
      C residues 5 to 21

<400> SEQUENCE: 14

Leu Ser Val Pro Asn Pro Leu Gly Phe Phe Pro Asp His Gln Leu Asp
1               5                   10                  15

Pro

<210> SEQ ID NO 15
<211> LENGTH: 7
<212> TYPE: PRT
<213> ORGANISM: Artificial Sequence
<220> FEATURE:
<223> OTHER INFORMATION: synthetic hepatitis B virus (HBV) preS
      genotype C residues 9 to 15

<400> SEQUENCE: 15

Asn Pro Leu Gly Phe Phe Pro
1               5

<210> SEQ ID NO 16
<211> LENGTH: 47
<212> TYPE: PRT
<213> ORGANISM: Artificial Sequence
<220> FEATURE:
<223> OTHER INFORMATION: synthetic hepatitis B virus (HBV) preS genotype
      D residues 2 to 48

<400> SEQUENCE: 16

Gly Gln Asn Leu Ser Thr Ser Asn Pro Leu Gly Phe Phe Pro Asp His
1               5                   10                  15

Gln Leu Asp Pro Ala Phe Arg Ala Asn Thr Ala Asn Pro Asp Trp Asp
            20                  25                  30

Phe Asn Pro Asn Lys Asp Thr Trp Pro Asp Ala Asn Lys Val Gly
        35                  40                  45

<210> SEQ ID NO 17
<211> LENGTH: 44

```
<212> TYPE: PRT
<213> ORGANISM: Artificial Sequence
<220> FEATURE:
<223> OTHER INFORMATION: synthetic hepatitis B virus (HBV) preS genotype
      D residues 5 to 48

<400> SEQUENCE: 17

Leu Ser Thr Ser Asn Pro Leu Gly Phe Phe Pro Asp His Gln Leu Asp
1               5                   10                  15

Pro Ala Phe Arg Ala Asn Thr Ala Asn Pro Asp Trp Asp Phe Asn Pro
            20                  25                  30

Asn Lys Asp Thr Trp Pro Asp Ala Asn Lys Val Gly
        35                  40

<210> SEQ ID NO 18
<211> LENGTH: 32
<212> TYPE: PRT
<213> ORGANISM: Artificial Sequence
<220> FEATURE:
<223> OTHER INFORMATION: synthetic hepatitis B virus (HBV) preS genotype
      D residues 2 to 33

<400> SEQUENCE: 18

Gly Gln Asn Leu Ser Thr Ser Asn Pro Leu Gly Phe Phe Pro Asp His
1               5                   10                  15

Gln Leu Asp Pro Ala Phe Arg Ala Asn Thr Ala Asn Pro Asp Trp Asp
            20                  25                  30

<210> SEQ ID NO 19
<211> LENGTH: 29
<212> TYPE: PRT
<213> ORGANISM: Artificial Sequence
<220> FEATURE:
<223> OTHER INFORMATION: synthetic hepatitis B virus (HBV) preS genotype
      D residues 5 to 33

<400> SEQUENCE: 19

Leu Ser Thr Ser Asn Pro Leu Gly Phe Phe Pro Asp His Gln Leu Asp
1               5                   10                  15

Pro Ala Phe Arg Ala Asn Thr Ala Asn Pro Asp Trp Asp
            20                  25

<210> SEQ ID NO 20
<211> LENGTH: 20
<212> TYPE: PRT
<213> ORGANISM: Artificial Sequence
<220> FEATURE:
<223> OTHER INFORMATION: synthetic hepatitis B virus (HBV) preS genotype
      D residues 2 to 21

<400> SEQUENCE: 20

Gly Gln Asn Leu Ser Thr Ser Asn Pro Leu Gly Phe Phe Pro Asp His
1               5                   10                  15

Gln Leu Asp Pro
            20

<210> SEQ ID NO 21
<211> LENGTH: 47
<212> TYPE: PRT
<213> ORGANISM: Artificial Sequence
<220> FEATURE:
<223> OTHER INFORMATION: synthetic hepatitis B virus (HBV) preS genotype
      C residues 2 to 48 with Ala substitututions at positions 21, 23,
      29 and 30

<400> SEQUENCE: 21
```

```
Gly Thr Asn Leu Ser Val Pro Asn Pro Leu Gly Phe Phe Pro Asp His
1               5                   10                  15

Gln Leu Asp Ala Ala Gly Ala Asn Ser Asn Ala Ala Asp Trp Asp
            20                  25                  30

Phe Asn Pro Asn Lys Asp His Trp Pro Glu Ala Asn Lys Val Gly
            35                  40                  45

<210> SEQ ID NO 22
<211> LENGTH: 59
<212> TYPE: PRT
<213> ORGANISM: Artificial Sequence
<220> FEATURE:
<223> OTHER INFORMATION: synthetic hepatitis B virus (HBV) preS
      genotype C positions (-11) to 48 with D20A substitutution

<400> SEQUENCE: 22

Met Gly Gly Trp Ser Ser Lys Pro Arg Gln Gly Met Gly Thr Asn Leu
1               5                   10                  15

Ser Val Pro Asn Pro Leu Gly Phe Phe Pro Asp His Gln Leu Ala Pro
            20                  25                  30

```
<212> TYPE: PRT
<213> ORGANISM: Artificial Sequence
<220> FEATURE:
<223> OTHER INFORMATION: synthetic hepatitis B virus (HBV) preS genotype
      C positions 2 to 48 with SNN(27-29)ANA substitututution

<400> SEQUENCE: 25

Gly Thr Asn Leu Ser Val Pro Asn Pro Leu Gly Phe Phe Pro Asp His
1               5                   10                  15

Gln Leu Asp Pro Ala Phe Gly Ala Asn Ala Asn Ala Pro Asp Trp Asp
            20                  25                  30

Phe Asn Pro Asn Lys Asp His Trp Pro Glu Ala Asn Lys Val Gly
        35                  40                  45

<210> SEQ ID NO 26
<211> LENGTH: 59
<212> TYPE: PRT
<213> ORGANISM: Artificial Sequence
<220> FEATURE:
<223> OTHER INFORMATION: synthetic hepatitis B virus (HBV) preS genotype
      C positions (-11) to 48 with D20A + SNN(27-29)ANA
      substitututions

<400> SEQUENCE: 26

Met Gly Gly Trp Ser Ser Lys Pro Arg Gln Gly Met Gly Thr Asn Leu
1               5                   10                  15

Ser Val Pro Asn Pro Leu Gly Phe Phe Pro Asp His Gln Leu Ala Pro
            20                  25                  30

Ala Phe Gly Ala Asn Ala Asn Ala Pro Asp Trp Asp Phe Asn Pro Asn
        35                  40                  45

Lys Asp His Trp Pro Glu Ala Asn Lys Val Gly
    50                  55

<210> SEQ ID NO 27
<211> LENGTH: 47
<212> TYPE: PRT
<213> ORGANISM: Artificial Sequence
<220> FEATURE:
<223> OTHER INFORMATION: synthetic hepatitis B virus (HBV) preS genotype
      C positions 2 to 48 with D20A + SNN(27-29)ANA
      substitututions

<400> SEQUENCE: 27

Gly Thr Asn Leu Ser Val Pro Asn Pro Leu Gly Phe Phe Pro Asp His
1               5                   10                  15

Gln Leu Ala Pro Ala Phe Gly Ala Asn Ala Asn Ala Pro Asp Trp Asp
            20                  25                  30

Phe Asn Pro Asn Lys Asp His Trp Pro Glu Ala Asn Lys Val Gly
        35                  40                  45

<210> SEQ ID NO 28
<211> LENGTH: 47
<212> TYPE: PRT
<213> ORGANISM: Artificial Sequence
<220> FEATURE:
<223> OTHER INFORMATION: synthetic hepatitis B virus (HBV) preS genotype
      D positions 2 to 48 with Ala substitututions at
      positions 21, 23, 29 and 30

<400> SEQUENCE: 28

Gly Gln Asn Leu Ser Thr Ser Asn Pro Leu Gly Phe Phe Pro Asp His
1               5                   10                  15

Gln Leu Asp Ala Ala Ala Arg Ala Asn Thr Ala Ala Ala Asp Trp Asp
            20                  25                  30
```

```
Phe Asn Pro Asn Lys Asp Thr Trp Pro Asp Ala Asn Lys Val Gly
        35                  40                  45

<210> SEQ ID NO 29
<211> LENGTH: 4
<212> TYPE: PRT
<213> ORGANISM: Artificial Sequence
<220> FEATURE:
<223> OTHER INFORMATION: synthetic hepatitis B virus (HBV) preS
      consensus sequence B-cell epitope motif residues 20 to 23

<400> SEQUENCE: 29

Asp Pro Ala Phe
1

<210> SEQ ID NO 30
<211> LENGTH: 7
<212> TYPE: PRT
<213> ORGANISM: Artificial Sequence
<220> FEATURE:
<223> OTHER INFORMATION: synthetic hepatitis B virus (HBV) preS
      consensus sequence or genotype C B-cell epitope motif
      residues 26 to 32

<400> SEQUENCE: 30

Asn Ser Asn Asn Pro Asp Trp
1               5

<210> SEQ ID NO 31
<211> LENGTH: 7
<212> TYPE: PRT
<213> ORGANISM: Artificial Sequence
<220> FEATURE:
<223> OTHER INFORMATION: synthetic hepatitis B virus (HBV) preS genotype
      D B-cell epitope motif residues 20 to 23

<400> SEQUENCE: 31

Asn Thr Ala Asn Pro Asp Trp
1               5

<210> SEQ ID NO 32
<211> LENGTH: 4
<212> TYPE: PRT
<213> ORGANISM: Artificial Sequence
<220> FEATURE:
<223> OTHER INFORMATION: synthetic hepatitis B virus (HBV) preS
      consensus sequence B-cell epitope motif residues 20 to 23
      modified by alanine substitution

<400> SEQUENCE: 32

Ala Pro Ala Phe
1

<210> SEQ ID NO 33
<211> LENGTH: 7
<212> TYPE: PRT
<213> ORGANISM: Artificial Sequence
<220> FEATURE:
<223> OTHER INFORMATION: synthetic hepatitis B virus (HBV) preS
      consensus sequence or genotype C B-cell epitope motif
      residues 26 to 32 modified by alanine
      substitutions

<400> SEQUENCE: 33

Asn Ala Asn Ala Pro Asp Trp
1               5
```

```
<210> SEQ ID NO 34
<211> LENGTH: 7
<212> TYPE: PRT
<213> ORGANISM: Artificial Sequence
<220> FEATURE:
<223> OTHER INFORMATION: synthetic hepatitis B virus (HBV) preS
      consensus sequence or genotype C B-cell epitope motif
      residues 26 to 32 modified by alanine
      substitutions

<400> SEQUENCE: 34

Asn Ala Ala Ala Pro Asp Trp
1               5

<210> SEQ ID NO 35
<211> LENGTH: 61
<212> TYPE: PRT
<213> ORGANISM: Artificial Sequence
<220> FEATURE:
<223> OTHER INFORMATION: synthetic hepatitis B virus (HBV) preS
      consensus sequence (positions (-11) to 50)

<400> SEQUENCE: 35

Met Gly Gly Trp Ser Ser Thr Pro Arg Lys Gly Met Gly Thr Asn Leu
1               5                   10                  15

Ser Val Pro Asn Pro Leu Gly Phe Phe Pro Asp His Gln Leu Asp Pro
            20                  25                  30

Ala Phe Arg Ala Asn Ser Asn Asn Pro Asp Trp Asp Phe Asn Pro Asn
        35                  40                  45

Lys Asp His Trp Pro Glu Ala Asn Lys Val Gly Val Gly
    50                  55                  60

<210> SEQ ID NO 36
<211> LENGTH: 61
<212> TYPE: PRT
<213> ORGANISM: Hepatitis B virus
<220> FEATURE:
<223> OTHER INFORMATION: hepatitis B virus (HBV) preS genotype A

<400> SEQUENCE: 36

Met Gly Gly Trp Ser Ser Lys Pro Arg Lys Gly Met Gly Thr Asn Leu
1               5                   10                  15

Ser Val Pro Asn Pro Leu Gly Phe Phe Pro Asp His Gln Leu Asp Pro
            20                  25                  30

Ala Phe Gly Ala Asn Ser Asn Asn Pro Asp Trp Asp Phe Asn Pro Val
        35                  40                  45

Lys Asp Asp Trp Pro Ala Ala Asn Gln Val Gly Val Gly
    50                  55                  60

<210> SEQ ID NO 37
<211> LENGTH: 61
<212> TYPE: PRT
<213> ORGANISM: Hepatitis B virus
<220> FEATURE:
<223> OTHER INFORMATION: hepatitis B virus (HBV) preS genotype B

<400> SEQUENCE: 37

Met Gly Gly Trp Ser Ser Lys Pro Arg Lys Gly Met Gly Thr Asn Leu
1               5                   10                  15

Ser Val Pro Asn Pro Leu Gly Phe Phe Pro Asp His Gln Leu Asp Pro
            20                  25                  30

Ala Phe Lys Ala Asn Ser Glu Asn Pro Asp Trp Asp Leu Asn Pro His
        35                  40                  45
```

```
Lys Asp Asn Trp Pro Asp Ala Asn Lys Val Gly Val Gly
        50                  55                  60

<210> SEQ ID NO 38
<211> LENGTH: 61
<212> TYPE: PRT
<213> ORGANISM: Artificial Sequence
<220> FEATURE:
<223> OTHER INFORMATION: synthetic hepatitis B virus (HBV) preS sequence
      positions

```
<400> SEQUENCE: 41

Met Gly Ala Pro Leu Ser Thr Thr Arg Arg Gly Met Gly Gln Asn Leu
 1               5                  10                  15

Ser Val Pro Asn Pro Leu Gly Phe Phe Pro Asp His Gln Leu Asp Pro
            20                  25                  30

Leu Phe Arg Ala Asn Ser Ser Pro Asp Trp Asp Phe Asn Thr Asn
        35                  40                  45

Lys Asp Ser Trp Pro Met Ala Asn Lys Val Gly Val Gly
    50                  55                  60

<210> SEQ ID NO 42
<211> LENGTH: 60
<212> TYPE: PRT
<213> ORGANISM: Hepatitis B virus
<220> FEATURE:
<223> OTHER INFORMATION: hepatitis B virus (HBV) preS genotype G

<400> SEQUENCE: 42

Met Gly Leu Ser Trp Thr Val Pro Leu Glu Trp Gly Lys Asn Leu Ser
 1               5                  10                  15

Ala Ser Asn Pro Leu Gly Phe Leu Pro Asp His Gln Leu Asp Pro Ala
            20                  25                  30

Phe Arg Ala Asn Thr Asn Asn Pro Asp Trp Asp Phe Asn Pro Lys Lys
        35                  40                  45

Asp Pro Trp Pro Glu Ala Asn Lys Val Gly Val Gly
    50                  55                  60

<210> SEQ ID NO 43
<211> LENGTH: 61
<212> TYPE: PRT
<213> ORGANISM: Hepatitis B virus
<220> FEATURE:
<223> OTHER INFORMATION: hepatitis B virus (HBV) preS genotype H

<400> SEQUENCE: 43

Met Gly Ala Pro Leu Ser Thr Ala Arg Arg Gly Met Gly Gln Asn Leu
 1               5                  10                  15

Ser Val Pro Asn Pro Leu Gly Phe Phe Pro Asp His Gln Leu Asp Pro
            20                  25                  30

Leu Phe Arg Ala Asn Ser Ser Ser Pro Asp Trp Asp Phe Asn Thr Asn
        35                  40                  45

Lys Asp Asn Trp Pro Met Ala Asn Lys Val Gly Val Gly
    50                  55                  60

<210> SEQ ID NO 44
<211> LENGTH: 50
<212> TYPE: PRT
<213> ORGANISM: Woolly Monkey Hepatitis B virus
<220> FEATURE:
<223> OTHER INFORMATION: woolly monkey hepatitis B virus (WMHBV) preS
      sequence

<400> SEQUENCE: 44

Met Gly Leu Asn Gln Ser Thr Phe Asn Pro Leu Gly Phe Phe Pro Ser
 1               5                  10                  15

His Gln Leu Asp Pro Leu Phe Lys Ala Asn Ala Gly Ser Ala Asp Trp
            20                  25                  30

Asp Lys Asn Pro Asn Lys Asp Pro Trp Pro Gln Ala His Asp Thr Ala
        35                  40                  45

Val Gly
```

<210> SEQ ID NO 45
<211> LENGTH: 14
<212> TYPE: PRT
<213> ORGANISM: Artificial Sequence
<220> FEATURE:
<223> OTHER INFORMATION: synthetic hepatitis B virus (HBV) preS genotype
      D residues 2 to 48

<400> SEQUENCE: 45

Gly Gln Asn Leu Ser Thr Ser Asn Pro Leu Gly Phe Phe Pro
1               5                   10

<210> SEQ ID NO 46
<211> LENGTH: 25
<212> TYPE: PRT
<213> ORGANISM: Artificial Sequence
<220> FEATURE:
<223> OTHER INFORMATION: synthetic hepatitis B virus (HBV) preS genotype
      D residues 2 to 26

<400> SEQUENCE: 46

Gly Gln Asn Leu Ser Thr Ser Asn Pro Leu Gly Phe Phe Pro Asp His
1               5                   10                  15

Gln Leu Asp Pro Ala Phe Arg Ala Asn
            20                  25

<210> SEQ ID NO 47
<211> LENGTH: 40
<212> TYPE: PRT
<213> ORGANISM: Artificial Sequence
<220> FEATURE:
<223> OTHER INFORMATION: synthetic hepatitis B virus (HBV) preS genotype
      D residues 9 to 48

<400> SEQUENCE: 47

Asn Pro Leu Gly Phe Phe Pro Asp His Gln Leu Asp Pro Ala Phe Arg
1               5                   10                  15

Ala Asn Thr Ala Asn Pro Asp Trp Asp Phe Asn Pro Asn Lys Asp Thr
            20                  25                  30

Trp Pro Asp Ala Asn Lys Val Gly
        35                  40

<210> SEQ ID NO 48
<211> LENGTH: 25
<212> TYPE: PRT
<213> ORGANISM: Artificial Sequence
<220> FEATURE:
<223> OTHER INFORMATION: synthetic hepatitis B virus (HBV) preS genotype
      D residues 9 to 33

<400> SEQUENCE: 48

Asn Pro Leu Gly Phe Phe Pro Asp His Gln Leu Asp Pro Ala Phe Arg
1               5                   10                  15

Ala Asn Thr Ala Asn Pro Asp Trp Asp
            20                  25

<210> SEQ ID NO 49
<211> LENGTH: 47
<212> TYPE: PRT
<213> ORGANISM: Artificial Sequence
<220> FEATURE:
<223> OTHER INFORMATION: synthetic hepatitis B virus (HBV) preS genotype
      D residues 10 to 48 (Ala2-9)

-continued

```
<400> SEQUENCE: 49

Ala Ala Ala Ala Ala Ala Ala Ala Pro Leu Gly Phe Phe Pro Asp His
1               5                   10                  15

Gln Leu Asp Pro Ala Phe Arg Ala Asn Thr Ala Asn Pro Asp Trp Asp
            20                  25                  30

Phe Asn Pro Asn Lys Asp Thr Trp Pro Asp Ala Asn Lys Val Gly
        35                  40                  45

<210> SEQ ID NO 50
<211> LENGTH: 47
<212> TYPE: PRT
<213> ORGANISM: Artificial Sequence
<220> FEATURE:
<223> OTHER INFORMATION: synthetic hepatitis B virus (HBV) preS genotype
      D residues 2 to 48 (Ala11-15)

<400> SEQUENCE: 50

Gly Gln Asn Leu Ser Thr Ser Asn Pro Ala Ala Ala Ala Ala Asp His
1               5                   10                  15

Gln Leu Asp Pro Ala Phe Arg Ala Asn Thr Ala Asn Pro Asp Trp Asp
            20                  25                  30

Phe Asn Pro Asn Lys Asp Thr Trp Pro Asp Ala Asn Lys Val Gly
        35                  40                  45

<210> SEQ ID NO 51
<211> LENGTH: 47
<212> TYPE: PRT
<213> ORGANISM: Artificial Sequence
<220> FEATURE:
<223> OTHER INFORMATION: synthetic hepatitis B virus (HBV) preS genotype
      D residues 2 to 48 (Ala17-21)

<400> SEQUENCE: 51

Gly Gln Asn Leu Ser Thr Ser Asn Pro Leu Gly Phe Phe Pro Asp Ala
1               5                   10                  15

Ala Ala Ala Ala Ala Phe Arg Ala Asn Thr Ala Asn Pro Asp Trp Asp
            20                  25                  30

Phe Asn Pro Asn Lys Asp Thr Trp Pro Asp Ala Asn Lys Val Gly
        35                  40                  45

<210> SEQ ID NO 52
<211> LENGTH: 42
<212> TYPE: PRT
<213> ORGANISM: Artificial Sequence
<220> FEATURE:
<223> OTHER INFORMATION: synthetic hepatitis B virus (HBV) preS genotype
      D residues 2 to 48 (delta11-15)

<400> SEQUENCE: 52

Gly Gln Asn Leu Ser Thr Ser Asn Pro Asp His Gln Leu Asp Pro Ala
1               5                   10                  15

Phe Arg Ala Asn Thr Ala Asn Pro Asp Trp Asp Phe Asn Pro Asn Lys
            20                  25                  30

Asp Thr Trp Pro Asp Ala Asn Lys Val Gly
        35                  40

<210> SEQ ID NO 53
<211> LENGTH: 42
<212> TYPE: PRT
<213> ORGANISM: Artificial Sequence
<220> FEATURE:
<223> OTHER INFORMATION: synthetic hepatitis B virus (HBV) preS genotype
      D residues 2 to 48 (delta17-21)
```

<400> SEQUENCE: 53

Gly Gln Asn Leu Ser Thr Ser Asn Pro Leu Gly Phe Phe Pro Asp Ala
1               5                   10                  15

Phe Arg Ala Asn Thr Ala Asn Pro Asp Trp Asp Phe Asn Pro Asn Lys
            20                  25                  30

Asp Thr Trp Pro Asp Ala Asn Lys Val Gly
        35                  40

<210> SEQ ID NO 54
<211> LENGTH: 47
<212> TYPE: PRT
<213> ORGANISM: Artificial Sequence
<220> FEATURE:
<223> OTHER INFORMATION: synthetic hepatitis B virus (HBV) preS genotype
      D residues 2 to 48 (Arg11)

<400> SEQUENCE: 54

Gly Gln Asn Leu Ser Thr Ser Asn Pro Arg Gly Phe Phe Pro Asp His
1               5                   10                  15

Gln Leu Asp Pro Ala Phe Arg Ala Asn Thr Ala Asn Pro Asp Trp Asp
            20                  25                  30

Phe Asn Pro Asn Lys Asp Thr Trp Pro Asp Ala Asn Lys Val Gly
        35                  40                  45

<210> SEQ ID NO 55
<211> LENGTH: 47
<212> TYPE: PRT
<213> ORGANISM: Artificial Sequence
<220> FEATURE:
<223> OTHER INFORMATION: synthetic hepatitis B virus (HBV) preS genotype
      D residues 2 to 48 (Glu12)

<400> SEQUENCE: 55

Gly Gln Asn Leu Ser Thr Ser Asn Pro Leu Glu Phe Phe Pro Asp His
1               5                   10                  15

Gln Leu Asp Pro Ala Phe Arg Ala Asn Thr Ala Asn Pro Asp Trp Asp
            20                  25                  30

Phe Asn Pro Asn Lys Asp Thr Trp Pro Asp Ala Asn Lys Val Gly
        35                  40                  45

<210> SEQ ID NO 56
<211> LENGTH: 47
<212> TYPE: PRT
<213> ORGANISM: Artificial Sequence
<220> FEATURE:
<223> OTHER INFORMATION: synthetic hepatitis B virus (HBV) preS genotype
      D residues 2 to 48 (Ser13)

<400> SEQUENCE: 56

Gly Gln Asn Leu Ser Thr Ser Asn Pro Leu Gly Ser Phe Pro Asp His
1               5                   10                  15

Gln Leu Asp Pro Ala Phe Arg Ala Asn Thr Ala Asn Pro Asp Trp Asp
            20                  25                  30

Phe Asn Pro Asn Lys Asp Thr Trp Pro Asp Ala Asn Lys Val Gly
        35                  40                  45

<210> SEQ ID NO 57
<211> LENGTH: 47
<212> TYPE: PRT
<213> ORGANISM: Artificial Sequence
<220> FEATURE:
<223> OTHER INFORMATION: synthetic hepatitis B virus (HBV) preS genotype D residues 2 to 48 (Ala18)

<400> SEQUENCE: 57

Gly Gln Asn Leu Ser Thr Ser Asn Pro Leu Gly Phe Phe Pro Asp His
1               5                   10                  15

Ala Leu Asp Pro Ala Phe Arg Ala Asn Thr Ala Asn Pro Asp Trp Asp
            20                  25                  30

Phe Asn Pro Asn Lys Asp Thr Trp Pro Asp Ala Asn Lys Val Gly
        35                  40                  45

<210> SEQ ID NO 58
<211> LENGTH: 58
<212> TYPE: PRT
<213> ORGANISM: Artificial Sequence
<220> FEATURE:
<223> OTHER INFORMATION: synthetic hepatitis B virus (HBV) preS
      consensus sequence (positions 2 to 59)

<400> SEQUENCE: 58

Gly Gly Trp Ser Ser Thr Pro Arg Lys Gly Met Gly Thr Asn Leu Ser
1               5                   10                  15

Val Pro Asn Pro Leu Gly Phe Phe Pro Asp His Gln Leu Asp Pro Ala
            20                  25                  30

Phe Arg Ala Asn Ser Asn Asn Pro Asp Trp Asp Phe Asn Pro Asn Lys
        35                  40                  45

Asp His Trp Pro Glu Ala Asn Lys Val Gly
        50                  55

<210> SEQ ID NO 59
<211> LENGTH: 47
<212> TYPE: PRT
<213> ORGANISM: Artificial Sequence
<220> FEATURE:
<223> OTHER INFORMATION: synthetic hepatitis B virus (HBV) preS
      scrambled

<400> SEQUENCE: 59

Thr Asn Asn Asp Pro Phe Lys Arg Thr Asp Leu Ala Trp Asn Gly Phe
1               5                   10                  15

Asp Ser Val Ala Gln Asn Asp Leu Leu Pro Asn Pro Pro Phe Asn Asn
            20                  25                  30

Trp Gly Asp Gly Ser His Gln Pro Ala Asp Ala Lys Pro Phe Thr
        35                  40                  45